United States Patent [19]

Hirota et al.

[11] 4,454,131

[45] Jun. 12, 1984

[54] THIOPHENE DERIVATIVES

[75] Inventors: Yojiro Hirota; Koichi Shinhama, both of Yamaguchi; Katsumi Sato; Takuo Wada, both of Kanagawa, all of Japan

[73] Assignees: Ube Industries, Ltd., Japan; Hokko Chemical Industry Co., Ltd., Japan

[21] Appl. No.: 488,684

[22] Filed: Apr. 26, 1983

[30] Foreign Application Priority Data

| Apr. 30, 1982 | [JP] | Japan | 57-71293 |
| Jul. 7, 1982 | [JP] | Japan | 57-116896 |
| Jul. 7, 1982 | [JP] | Japan | 57-116897 |
| Jul. 7, 1982 | [JP] | Japan | 57-116898 |
| Feb. 8, 1983 | [JP] | Japan | 58-18069 |
| Feb. 23, 1983 | [JP] | Japan | 58-27753 |

[51] Int. Cl.$^3$ ............... A01N 43/84; A01N 43/02; C07D 409/00; C07D 413/00
[52] U.S. Cl. ............... 424/248.51; 424/244; 424/263; 424/267; 424/274; 424/275; 260/239 E; 260/239 A; 544/146; 546/212; 546/213; 546/284; 548/527; 549/59; 549/60; 549/64
[58] Field of Search ............... 424/244, 248.51, 263, 424/267, 274, 275; 260/239 E, 239 A; 542/427; 544/146; 546/212, 213, 284; 548/527; 549/59, 60, 64

[56] References Cited

U.S. PATENT DOCUMENTS 2,438,808  3/1948  Avison et al. ............... 549/64
2,453,102  11/1948  Turnbull ............... 549/64

OTHER PUBLICATIONS

Chemical Abstracts 79:42266c (1973).

Primary Examiner—Alan Siegel
Attorney, Agent, or Firm—Abelman, Frayne, Rezac & Schwab

[57] ABSTRACT

This invention relates to new thiophene derivatives and their use as fungicides in agriculture and horticulture.

2 Claims, No Drawings

THIOPHENE DERIVATIVES

The new thiophene derivatives according to the present invention are represented by the general formula (I).

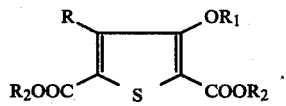

In the general formula: R is $C_{1-4}$-alkyl; $R_1$ is

wherein $R_3$ is $C_{1-4}$-alkyl, halogen-substituted $C_{1-4}$-alkyl, $C_{2-4}$-alkenyl, $C_{3-8}$-cycloalkyl, $C_{1-4}$-alkoxy-$C_{1-4}$-alkyl, $C_{1-4}$-alkylthio-$C_{1-4}$-alkyl, $C_{1-4}$-alkoxycarbonyl-$C_{1-4}$-alkyl, $C_{1-10}$-alkoxy, $C_{1-4}$-alkynyloxy, styryl, α-phenoxyethyl, thienyl, furyl, 2,3-dibromopropyloxy, a group

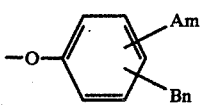

(wherein A and B individually are halogen, $C_{1-4}$-alkyl, methoxy or methylthio, and m and n individually are 0 or 1 with the proviso m+n cannot exceed 2), mono-$C_{1-4}$-alkylamino, di-$C_{1-4}$-alkylamino, mono-$C_{3-8}$-cycloalkylamino, monoaralkylamino, diphenylamino, a group

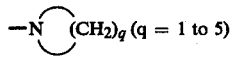

which may be substituted with one or two $C_{1-4}$-alkyl; a group

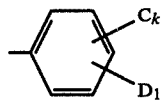

(wherein C is a halogen atom, D is $C_{1-4}$-alkyl, $C_{1-4}$-alkoxy, $C_{1-4}$-alkylcarboxy, nitro or cyano, k is 0, 1 or 2 and l is 0, 1, 2 or 3); $C_{1-4}$-alkylthio; $C_{1-4}$-alkenylthio; $C_{1-4}$-alkoxycarbonyl-$C_{1-4}$-alkylthio; aralkylthio or $C_{1-4}$-alkyl-substituted aralkylthio; aralkyl which phenyl portion may be substituted with halogen or $C_{1-4}$-alkoxy; a group

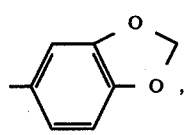

phenoxy-$C_{1-4}$-alkyl which phenyl portion may be substituted with halogen; pyridine-4-yl; or a group

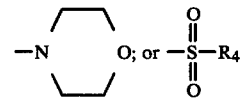

wherein $R_4$ is $C_{1-6}$-alkyl, di-$C_{1-4}$-alkylamino or a group

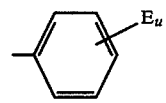

(in which E is halogen or $C_{1-4}$-alkyl and μ is 0 or 1); $R_2$ is $C_{1-4}$-alkyl or $C_{2-4}$-alkenyl; provided that;

(a) When $R_3$ is mono-$C_{3-8}$-cycloalkylamino, $R_2$ represents $C_{1-4}$-alkoxy-$C_{1-4}$-alkyl, aralkyl, phenoxy-$C_{1-4}$-alkyl or $C_{2-4}$-alkynyl;

(b) When $R_3$ is

$R_2$ represents $C_{1-4}$-alkoxy-$C_{1-4}$-alkyl or aralkyl;

(c) When $R_3$ is

$R_2$ represents $C_{3-8}$-cycloalkyl; and (d) When $R_3$ is $C_{1-4}$-alkylthio, $R_2$ represents $C_{1-4}$-alkoxy-$C_{1-4}$-alkyl, aralkyl or phenoxy-$C_{1-4}$-alkyl.

A number of thiophene derivatives have been synthesized by us for investigation of their utility as fungicides in agriculture and horticulture. Consequently, new compounds of the above general formula (I) are found effective against various plant diseases such as rice blast, rice brown spot, rice sheath blight, tomato late blight, haricot sclerotinia rot, rice 'Bakanae' disease, cucumber Fusarium wilt, tomato leaf mold, grape ripe rot, pear black spot, Japanese apple canker, vegetable soft rot, rice bacterial blight, cucumber bacterial spot, cucumber downy mildew, cucumber powdery mildew, cucumber anthracnose, etc. They are further useful for controlling powdery mildew and root knot diseases of various crops, vegetables, flowers and fruit trees, as well as phytophthora rot of soybean, adzuki bean and broad bean, phytophthora blight of taro, phytophthora damping off of cucumber, phytophthora rot of oriental melon, netted melon and oriental pickling melon, brown rot of water melon, phytophthora rot of pumpkin, phytophthora rot of bottle gourd, brown rot of egg plant, phytophthora blight of sweet pepper, red stele of strawberry, phytophthora rot of onion, phytophthora blight of Welsh onion, pythium blight of wheat or barley.

The compounds of the general formula (I) can be prepared by the following reactions:

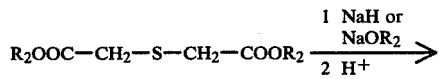

(1)

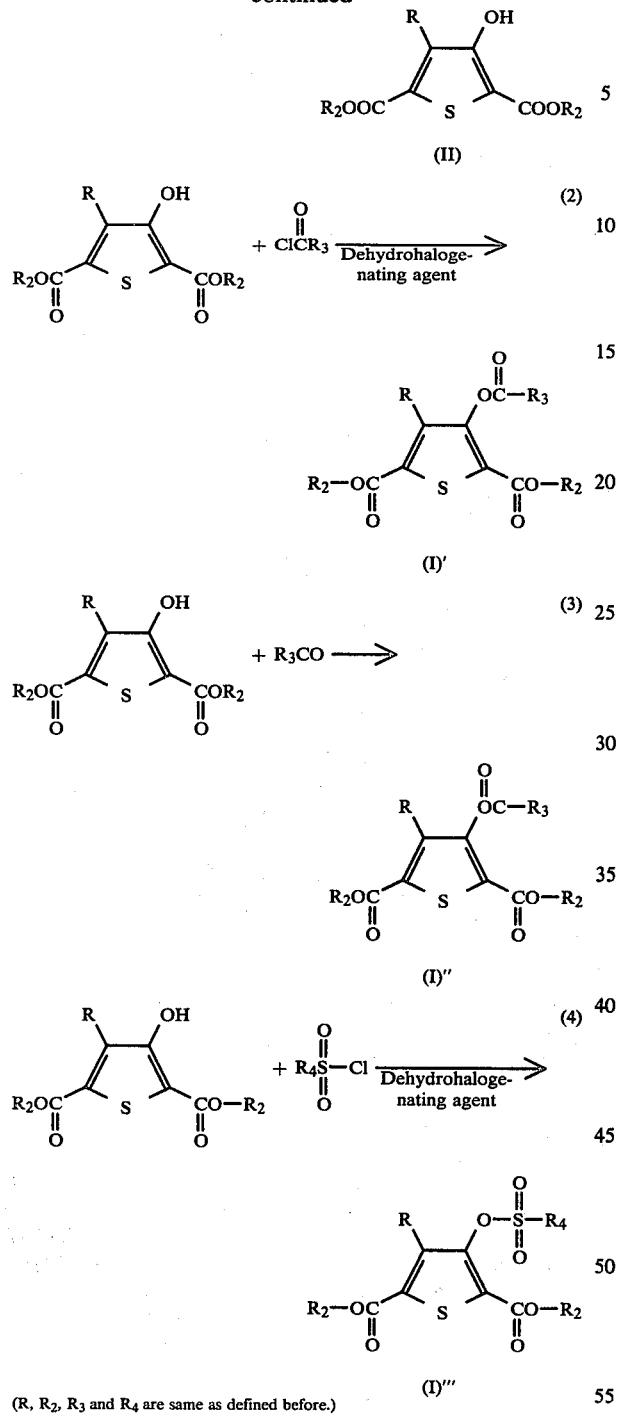

(R, R₂, R₃ and R₄ are same as defined before.)

The reaction (1) can be carried out in an organic solvent such as alcohol, ether, hydrocarbon, dimethyl formamide, etc., in the presence of a deprotonating agent such as metal sodium, NaH, butyl lithium, alcoholate, etc., at a temperature of 0°–100° C. for 2–24 hours. The resulting reaction mixture is poured into ice water and then worked up with a mineral acid like hydrochloric or sulfuric acid.

The reaction (2) or (4) can be carried out in an inert solvent such as dioxane, acetone, benzene, dimethyl formamide, etc., in the presence of a dehydrohalogenating agent such as triethylamine, pyridine, potassium or sodium carbonate, etc., at a temperature of 0°–100° C. for 1–24 hours. The resulting reaction mixture is poured into water and then worked up as by filtration, extraction, etc.

The reaction (3) can be carried out in an inert organic solvent such as dioxane, ethylether, hydrocarbon, benzene, etc., in the presence of a catalyst such as triethylamine, pyridine, etc., at a temperature of 20°–80° C. for 1–5 days. The reaction mixture obtained is worked up by distillation to remove the solvent and recrystallization.

The following examples are given to show the typical procedures for the preparation of the compounds of the present invention, without limiting the scope of the invention thereto.

EXAMPLE 1

Di-isopropyl 3-methyl-4-hydroxy-2,5-thiophenedicarboxylate

Sodium hydride (132 g, 5.52 mol) was added gradually into isopropyl alcohol (2–3 l) with cooling. To the resulting solution was then added a mixture of isopropyl pyruvate (360 g, 2.76 mol) and di-isopropyl 2,2'-thiodiglycolate (648 g, 2.76 mol) over 20–30 minutes with ice-cooling so that the solution was kept at 60°–80° C. The solution was stirred further for 2 hours at a temperature of 60°–40° C. The solution was poured into an ice-cooled dilute hydrochloric acid solution to form a white crystalline mass, which was recovered by filtration and then washed with water. It was recrystallized from methanol (3 l) to give pure di-isopropyl 3-methyl-4-hydroxy-2,5-thiophene-dicarboxylate (270 g, 34%), m.p. 87°–89° C.

IR(nujol): 3280, 1700, 1660, 1560, 1355, 1210, 1155, 1090, 910, 760 cm⁻¹. NMR(CDCl₃): 1.40(d, J=7 Hz, 12H,

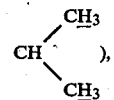
), 2.43 (s, 3H, —CH₃), 5.1–5.5(m, 2H,

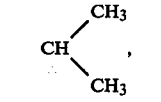
, 9.77 ppm (s, 1H, —OH).

EXAMPLE 2

Di-isopropyl 3-methyl-4-benzoyloxy-2,5-thiophene dicarboxylate (Compound No. 4)

A mixture of di-isopropyl 3-methyl-4-hydroxy-2,5-thiophene-dicarboxylate (656 g, 2.30 mol), triethylamine (297 g, 2.98 mol) and dioxane (2 l) was cooled with ice to about 10° C. The solution was added, while stirring, with benzoyl chloride (351 g, 2.5 mol) over about 10 minutes, followed by further stirring for 30 minutes at room temperature. After removing the precipitate of triethylamine hydrochloride salt by filtration, the solution was distilled in vacuo to remove dioxane. Toluene was then added to the remaining residue, and the solution was washed with 5% aqueous sodium bicarbonate and water, and then dried over MgSO₄. The solvent was removed by distillation to give almost pure di-isopropyl 3-methyl-4-benzoyloxy-2,5-thiophene dicarboxylate (851 g, 95%). $n_D^{10}$ 1.5499.

IR(neat): 1750, 1700, 1600, 1010, 965, 910, 762, 700 cm$^{-1}$. NMR(CDCl$_3$): 1.15(d, J=7 Hz, 6H,

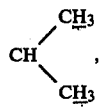

1.40(d, J=7 Hz, 6H,

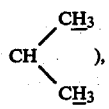

2.42 (s, 3H, CH$_3$), 5.0–5.4 (m, 2H,

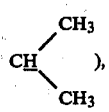

7.3–8.4 ppm (m, 5H).

EXAMPLE 3

Di-isopropyl 3-methyl-4-(4-nitrobenzoyloxy)-2,5-thiophene-dicarboxylate (Compound No. 46)

1.1 g (4 mmol) of di-isopropyl 3-methyl-4-oxy-2,5-thiophene dicarboxylate and 1 g (10 mmol) of triethylamine were dissolved into 6 ml of dioxane, and the resulting solution was ice-cooled with stirring, and then added with 1.1 g (6 mmol) of 4-nitro benzoyl chloride. The mixture was allowed to stand overnight, then added with 30 ml of 5% aqueous NaHCO$_3$, extracted with 30 ml of ethylether, and washed with water 2 or 3 times. The extract was dried over MgSO$_4$, and distilled to remove the solvent. The crude product obtained was recrystallized from about 5 ml of methyl alcohol to give the Compound No. 46 (1.6 g, 92%) in the white crystalline form.

IR (nujol): 1760(C=O), 1715(C=O), 1523, 1370, 1350, 710 cm$^{-1}$. NMR(CDCl$_3$): δ1.20(d, J=7 Hz, 6H —CH(CH$_3$)$_2$), 1.38(d, J=7 Hz, 6H, —CH(CH$_3$)$_2$), 2.40(s, 3H, —CH$_3$), 4.9–5.4(m, 2H, —CH(CH$_3$)$_2$), 8.35(br, 4H, ring proton).

EXAMPLE 4

Dipropyl 3-methyl-4-(4-methoxybenzoyloxy)-2,5-thiophenedicarboxylate (Compound No. 58)

1.1 g (4 mmol) of dipropyl 3-methyl-4-oxy-2,5-thiophene-dicarboxylate and 1 g (10 mmol) of triethylamine were dissolved into 6 ml of dioxane to obtain a solution, to which was added dropwise 1.0 g (6 mmol) of 4-methoxybenzoyl chloride while the solution was stirred with ice-cooling. Thereafter, the mixture was allowed to stand overnight at room temperature. Then the reaction mixture was added with 30 ml of 5% aqueous NaHCO$_3$, extracted with 30 ml of ethylether, and washed with water 2 to 3 times. The extract was dried with MgSO$_4$ and then distilled to remove the solvent. The Compound No. 58 is obtained as an almost pure yellowish viscous liquid (1.1 g, 65%).

IR(neat): 1740(C=O), 1710(C=O), 1605, 850, 770 cm$^{-1}$. NMR(CDCl$_3$): δ0.85(t, 3H, —CH$_2$CH$_2$CH$_3$), 1.02 (t, 3H, —CH$_2$CH$_2$CH$_3$), 1.4–2.0(m, 4H, —CH$_2$CH$_2$CH$_3$),

3.85(s, 3H, OCH$_3$), 4.10 (t, 2H, —CH$_2$CH$_2$CH$_3$), 4.25(t, 2H, —CH$_2$CH$_2$CH$_3$), 6.95(d, J=SHz, 2H, ring proton), 8.13(d, J=8 Hz, 2H, ring proton).

EXAMPLE 5

Dimethyl 3-methyl-4-butylthio-carbonyloxy-2,5-thiophene dicarboxylate (Compound No. 78)

1.8 g (8 mmol) of dimethyl 3-methyl-4-oxy-2,5-thiophene dicarboxylate and 4 g (40 mmol) of triethylamine were dissolved into 40 ml of dioxane, and 1.8 g (12 mmol) of S-butyl chloro-thioformate was added dropwise to the solution thus obtained, while it was ice-cooled with stirring. After the addition, the mixture was allowed to stand overnight at at room temperature, added with 50 ml of 5% aqueous NaHCO$_3$, extracted with 50 ml of ethylether and then washed 2 to 3 times with water. The extract was dried with MgSO$_4$, and distilled to remove the solvent. The compound No. 78 was obtained (2.2 g, 79%).

IR(neat): 1720(C=O), 1260, 1070, 770 cm$^{-1}$. NMR(CDCl$_3$): δ0.95(t, 3H, —CH$_2$CH$_2$CH$_2$CH$_3$), 1.1–1.8(m, 4H, —CH$_2$CH$_2$CH$_2$CH$_3$),

2.95 (t, 2H, —CH$_2$CH$_2$CH$_2$CH$_3$), 3.90(s, 6H, CO=CH$_3$).

EXAMPLE 6

Di-isopropyl 3-methyl-4-(4-methylbenzylthiocarbonyloxy)-2,5-thiophene-dicarboxylate (Compound No. 94)

2.3 g (8 mmol) of di-isopropyl 3-methyl-4-oxy-2,5-thiophene-dicarboxylic and 2 g (20 mmol) of triethylamine were dissolved into 20 ml of dioxane to form a solution, to which was added dropwise, while stirring with cooling with ice, 2.4 g (12 mmol) of S-4-methyl-benzyl chloro-thioformate. After the addition, the mixture was allowed to stand overnight at room temperature, added 50 ml of 5% aqueous NaHCO$_3$, extracted with 50 ml of ethylether, and then washed 2 to 3 times with water. The extract was dried over MgSO$_4$ and distilled to remove the solvent thereby to give the compound No. 94 as an almost pure yellowish viscous liquid (3.2 g, 89%).

IR(neat): 1730(C=O), 1720(C=O), 1320, 1285, 1125, 800 cm$^{-1}$. NMR(CDCl$_3$): δ1.35(t, 12H, —CH(CH$_3$)$_2$),

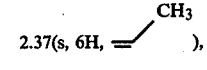

4.24(s, 2H, —SCH$_2$), 5.1–5.5 (m, 2H, —CH(CH$_3$)$_2$), 7.1–7.5(m, 4H, ring proton).

EXAMPLE 7

Di-ethyl 3-methyl-4-methylcarbamoyloxy-2,5-thiophene-dicarboxylate (Compound No. 99)

5.2 g (20 mmol) of diethyl 3-methyl-4-hydroxy-2,5-thiophene dicarboxylate was dissolved in 60 ml of dioxane to form a solution, to which was added dropwise 1.7 g (30 mmol) of methyl isocyanate. The mixture was allowed to stand overnight at room temperature, to which was then added n-hexane. The white crystalline mass separated was recovered by filtration and then washed with n-hexane. It was dried in vacuo to give 5.5 g (87%) of the desired carbamic acid ester.

IR(nujol): 3300(NH), 1710(C=O), 1290, 1250 cm$^{-1}$. NMR(CDCl$_3$): δ1.2–1.3(m, 6H, —CH$_2$CH$_3$),

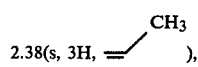

2.38(s, 3H,            ), 2.94(d, J=6 Hz, 3H, NHCH$_3$), 4.2–4.5 (m, 4H, —CH$_2$CH$_3$), 5.1–5.4(br, 1H, NH).

EXAMPLE 8

Diethyl 3-methyl-4-dimethylcarbamoyloxy-2,5-thiophene-dicarboxylate (Compound No. 116)

5.2 g (20 mmol) of diethyl 3-methyl-4-hydroxy-2,5-thiophene dicarboxylate was dissolved in a mixture of 40 ml of dioxane and 20 ml of pyridine to form a solution, to which was added dropwise 3.2 g (30 mmol) of dimethyl carbamoyl chloride. The reaction mixture was stirred overnight and then poured into cold water, acidified with hydrochloric acid, extracted with ethylether and then dried over anhydrous magnesium sulfate. The solvent was removed by distillation, and the crude product was recrystallized by use of a mixed solvent of ethanol and hexane to give 5.2 g (79%) of the desired carbamic acid ester.

IR(nujol): 1710(C=O), 1690(C=O), 1370, 1250, 1140, 1360, 765 cm$^{-1}$. NMR(CDCl$_3$): δ1.2–1.5(m, 6H, —CH$_2$—CH$_3$),

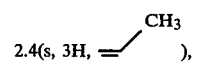

2.4(s, 3H,            ), 3.05(s, 3H, N—CH$_3$), 3.18(s, 3H, N—CH$_3$), 4.2–4.5(m, 4H, CH$_2$—CH$_3$).

EXAMPLE 9

Dimethyl 3-methyl-4-acetoxy-2,5-thiophenedicarboxylate (Compound No. 189)

1.2 g (5 mmol) of dimethyl 3-methyl-4-oxy-2,5-thiophene-dicarboxylate and 1.3 g of triethylamine were dissolved into 20 ml of dioxane to form a solution, to which was added 0.6 g (7.5 mmol) of acetyl chloride while stirring the solution with ice-cooling. Further, the mixture was stirred for 2 hours at room temperature, added with 30 ml of 5% aqueous NaHCO$_3$, extracted with 30 ml of ethylether, and then washed 2 to 3 times with water. The extract was dried over anhydrous magnesium sulfate and then distilled to remove the solvent to give a crude product, which was recrystallized from about 5 ml of methyl alcohol to give as a crystalline white mass the compound No. 189. Yield 10 g (70%).

IR(nujol): 1765(C=O), 1710(C=O), 1690(C=O), 1300, 1255, 1180, 1055 cm$^{-1}$. NMR(CDCl$_3$):

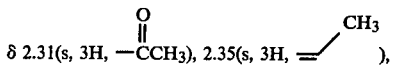

3.80(s, 3H, —CO$_2$CH$_3$), 3.83(s, 3H, —CO$_2$CH$_3$).

EXAMPLE 10

Diethyl 3-methyl-4-(3-methylcrotonoyloxy)-2,5-thiophene dicarboxylate (Compound No. 219)

2.1 g (8 mmol) of diethyl 3-methyl-4-oxy-2,5-thiophene dicarboxylate and 2 g of triethylamine were dissolved in 30 ml of dioxane to give a solution, to which was added 1.4 g (12 mmol) of 3-methyl-crotonyl chloride while stirring and ice-cooling. Further, the mixture was stirred for 2 hours at room temperature, added with 30 ml of 5% aqueous NaHCO$_3$, extracted with 30 ml of ethylether, and washed with water 2 to 3 times. The extract was dried over anhydrous magnesium sulfate and distilled to remove the solvent. The crude product obtained was purified by silica gel column chromatography (hexane/ethyl ether=10:1). Yield 2.1 g (77%).

IR(KBr): 1742(C=O), 1715(C=O), 1695(C=O), 1640(C=C), 1293, 1248, 1105, 1070 cm$^{-1}$. NMR(CDCl$_3$): δ1.2–1.5(m, 6H, —CH$_2$CH$_3$),

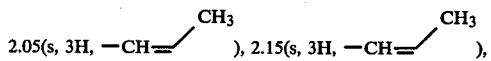

2.40 (s, 3H, ring —CH$_3$), 4.3–4.6(m, 4H, —CH$_2$CH$_3$),

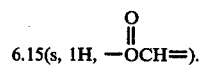

6.15(s, 1H, —OCH=).

EXAMPLE 11

Di-isopropyl 3-methyl-4-butane sulfonyloxy-2,5-thiophene-dicarboxylate (Compound No. 315)

A mixture of 2.3 g (8 mmol) of di-isopropyl 3-methyl-4-hydroxy-2,5-thiophene-dicarboxylate, 30 ml of dioxane, 60 ml of acetone, 1.6 g (120 mmol) of anhydrous potassium carbonate and 1.6 g (10 mmol) of butane-sulfonyl chloride was refluxed for about 10 hours. The mixture was then freed from dioxane and acetone by distillation in vacuo and then added with ethylether, washed with water, and dried with anhydrous magnesium sulfate. The solvent was removed by distillation and then recrystallization was effected from methanol to give 2.8 g (86%) of the desired white crystalline compound. m.p. 59°–61° C.

IR(nujol): 1720(C=O), 1255, 1150, 1110 cm$^{-1}$. NMR(CDCl$_3$): δ1.00(t, 3H, —CH$_2$—CH$_3$), 1.35(d, J=7 Hz, 12H), 1.5–2.2(m, 4H, —CH$_2$—CH$_2$—),

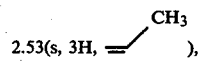

3.61(t, 2H, —SO$_2$—CH$_2$—), 5.0–5.4(m, 2H, —CCH—)

EXAMPLE 12

Dipropyl 3-methyl-4-(4-bromobenzene-sulfonyloxy)-2,5-thiophene-dicarboxylate (Compound No. 332)

A mixture of 2.3 g (8 mmol) of dipropyl 3-methyl-4-hydroxy-2,5-thiophene-dicarboxylate, 20 ml of dioxane, 40 ml of acetone, 1.6 g (12 mmol) of anhydrous potassium carbonate and 2.3 g (10 mmol) of 4-bromobenzene-sulfonyl chloride was refluxed for about 10 hours, removed of dioxane and acetone by distillation, added with ethyl ether, washed with water, and dried with anhydrous magnesium sulfate. The solvent was removed by distillation, and recrystallization was effected with use of methanol to give 3.8 g (94%) of the desired white crystalline compound, m.p. 73°–74° C.

IR(nujol): 1700(C=O), 1570, 1290, 1185, 1060, 790, 770 cm$^{-1}$. NMR(CDCl$_3$): $\delta$0.90–1.18(m, 6H, —CH$_2$CH$_2$CH$_3$), 1.5–2.0(m 4H, —CH$_2$CH$_2$—), 2.25(s, 3H, =CH$_3$), 4.0–4.4(m, 4H, C—CH$_2$—), 7.58–7.90(m, 4H, ring proton).

Exemplified below in Tables 1a and 1b are the compounds of the present invention as prepared in accordance with the procedures described in the foregoing examples. The compound number assigned to each compounds in the tables will be referred to in the examples and test examples that follow.

TABLE 1a

| Compound No. | R | R$_3$ | R$_2$ | Physicochemical data m.p. (°C.) or refractive index n$_D$ |
|---|---|---|---|---|
| 1 | CH$_3$— |  | CH$_3$— | m.p. 96–98 |
| 2 | " | " | C$_2$H$_5$— | m.p. 78–80 |
| 3 | " | " | nC$_3$H$_7$— | n$_D^{10}$ 1.5582 |
| 4 | " | " | iC$_3$H$_7$— | n$_D^{16}$ 1.5499 |
| 5 | " | " | nC$_4$H$_9$— | n$_D^{16}$ 1.5468 |
| 6 | " | " | iC$_4$H$_9$— | n$_D^{16}$ 1.5441 |
| 7 | " | " | CH$_2$=CHCH$_2$— | m.p. 54–55 |
| 8 | " | 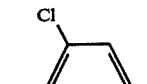 | C$_2$H$_5$— | m.p. 98–100 |
| 9 | " | " | nC$_3$H$_7$— | m.p. 90–91 |
| 10 | " | " | iC$_3$H$_7$— | n$_D^{18}$ 1.5566 |
| 11 | " | " | nC$_4$H$_9$— | n$_D^{17}$ 1.5532 |
| 12 | " | " | iC$_4$H$_9$— | m.p. 99–100 |
| 13 | " | 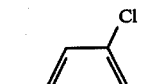 | nC$_3$H$_7$— | n$_D^{12}$ 1.5652 |
| 14 | " | " | iC$_3$H$_7$— | n$_D^{12}$ 1.5589 |
| 15 | " | " | nC$_4$H$_9$— | n$_D^{12}$ 1.5605 |
| 16 | " | 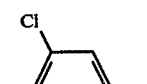 | nC$_3$H$_7$— | n$_D^{12}$ 1.5626 |
| 17 | " | " | iC$_3$H$_7$— | n$_D^{12}$ 1.5590 |
| 18 | " | " | nC$_4$H$_9$— | n$_D^{15}$ 1.5577 |
| 19 | " | 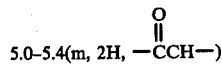 | C$_2$H$_5$— | m.p. 97–99 |
| 20 | " | " | nC$_3$H$_7$— | m.p. 56–58 |
| 21 | " | " | iC$_3$H$_7$— | n$_D^{10}$ 1.5701 |
| 22 | " | " | nC$_4$H$_9$— | n$_D^{15}$ 1.5605 |

TABLE 1a-continued $$\underset{\underset{O}{R_2OC}}{\overset{R}{\underset{\|}{\overset{\|}{\diagdown}}}}\underset{S}{\overset{O}{\underset{\|}{\overset{\|}{\underset{\|}{\diagdown}}}}}\underset{\overset{\|}{O}}{\overset{OC-R_3}{\diagup}}COR_2$$

| Compound No. | R | $R_3$ | $R_2$ | Physicochemical data m.p. (°C.) or refractive index $n_D$ |
|---|---|---|---|---|
| 23 | " | 3,4-diCl-C$_6$H$_3$ | nC$_3$H$_7$— | m.p. 52–55 |
| 24 | " | " | iC$_3$H$_7$— | $n_D^{12}$ 1.5705 |
| 25 | " | " | nC$_4$H$_9$— | $n_D^{15}$ 1.5778 |
| 26 | C$_2$H$_5$— | C$_6$H$_5$ | iC$_3$H$_7$— | $n_D^{10}$ 1.5489 |
| 27 | nC$_3$H$_7$— | " | iC$_3$H$_7$— | $n_D^{10}$ 1.5459 |
| 28 | CH$_3$— | 4-F-C$_6$H$_4$ | " | $n_D^{12}$ 1.5418 |
| 29 | " | 4-I-C$_6$H$_4$ | " | m.p. 77–79 |
| 30 | " | 2-Br-C$_6$H$_4$ | " | $n_D^{12}$ 1.5674 |
| 31 | " | 4-CH$_3$-C$_6$H$_4$ | C$_2$H$_5$— | m.p. 84–85° C. |
| 32 | " | " | n-C$_3$H$_7$— | m.p. 55–57° C. |
| 33 | " | " | i-C$_3$H$_7$— | $n_D^{16}$ 1.5490 |
| 34 | " | " | n-C$_4$H$_9$— | $n_D^{16}$ 1.5470 |
| 35 | " | " | i-C$_4$H$_9$— | m.p. 74–75° C. |
| 36 | " | 3-CH$_3$-C$_6$H$_4$ | n-C$_3$H$_7$— | $n_D^{15}$ 1.5536 |
| 37 | " | " | i-C$_3$H$_7$— | m.p. 87° C. |
| 38 | " | " | n-C$_4$H$_9$— | $n_D^{15}$ 1.5479 |
| 39 | " | 2-CH$_3$-C$_6$H$_4$ | n-C$_3$H$_7$— | $n_D^{15}$ 1.5545 |
| 40 | " | " | i-C$_3$H$_7$— | $n_D^{15}$ 1.5494 |
| 41 | " | " | n-C$_4$H$_9$— | $n_D^{15}$ 1.5487 |
| 42 | " | 4-t-C$_4$H$_9$-C$_6$H$_4$ | n-C$_3$H$_7$— | $n_D^{12}$ 1.5483 |
| 43 | " | " | i-C$_3$H$_7$— | m.p. 96–98° C. |
| 44 | " | " | n-C$_4$H$_9$— | $n_D^{15}$ 1.5417 |

TABLE 1a-continued $$\text{R}_2\text{OC}-\underset{\underset{S}{}}{\overset{R}{\diagup}}\overset{O-\overset{O}{C}-R_3}{\diagdown}-\text{COR}_2$$

| Compound No. | R | R₃ | R₂ | Physicochemical data m.p. (°C.) or refractive index $n_D$ |
|---|---|---|---|---|
| 45 | " | ⌬-NO₂ (para) | n-C₃H₇— | m.p. 90–91° C. |
| 46 | " | " | i-C₃H₇— | m.p. 134–135° C. |
| 47 | " | " | n-C₄H₉— | m.p. 63–65° C. |
| 48 | " | ⌬-NO₂ (meta) | n-C₃H₇— | $n_D^{12}$ 1.5659 |
| 49 | " | " | i-C₃H₇— | $n_D^{12}$ 1.5626 |
| 50 | " | " | n-C₄H₉— | m.p. 58–60° C. |
| 51 | " | 2,4-(NO₂)₂-C₆H₃— | C₂H₅— | m.p. 100–101° C. |
| 52 | " | 2-Cl-4-NO₂-C₆H₃— | n-C₃H₇— | m.p. 48–51° C. |
| 53 | " | " | i-C₃H₇— | m.p. 93–95° C. |
| 54 | " | " | n-C₄H₉— | $n_D^{15}$ 1.5606 |
| 55 | " | 2-Cl-4-NO₂-C₆H₃— (3-Cl isomer) | n-C₃H₇— | m.p. 84–85° C. |
| 56 | " | " | i-C₃H₇— | m.p. 97–100° C. |
| 57 | " | " | n-C₄H₉— | m.p. 61–63° C. |
| 58 | " | 4-OCH₃-C₆H₄— | n-C₃H₇— | $n_D^{12}$ 1.5650 |
| 59 | " | " | i-C₃H₇— | $n_D^{12}$ 1.5602 |
| 60 | " | " | n-C₄H₉— | $n_D^{15}$ 1.5551 |
| 61 | " | 2-OCH₃-C₆H₄— | n-C₃H₇— | $n_D^{12}$ 1.5692 |
| 62 | " | " | i-C₃H₇— | $n_D^{12}$ 1.5632 |
| 63 | " | 2,6-(OCH₃)₂-C₆H₃— | " | $n_D^{12}$ 1.5492 |

TABLE 1a-continued $$\text{R}_2\text{OC}-\underset{\underset{S}{\phantom{x}}}{\overset{R}{\underset{\|}{C}}}=\overset{OC(O)R_3}{\underset{COR_2}{C}}$$

| Compound No. | R | $R_3$ | $R_2$ | Physicochemical data m.p. (°C.) or refractive index $n_D$ |
|---|---|---|---|---|
| 64 | " | 3,4,5-tri(OCH$_3$)-C$_6$H$_2$— | i-C$_3$H$_7$— | $n_D^{12}$ 1.5666 |
| 65 | " | 4-(OCOCH$_3$)-C$_6$H$_4$— | " | $n_D^{12}$ 1.5480 |
| 66 | C$_2$H$_5$— | 4-CH$_3$-C$_6$H$_4$— | " | $n_D^{10}$ 1.5490 |
| 67 | " | 2-CH$_3$-C$_6$H$_4$— | " | $n_D^{10}$ 1.5482 |
| 68 | CH$_3$ | n-C$_3$H$_7$S— | C$_2$H$_5$— | m.p. 45–46 |
| 69 | " | " | n-C$_3$H$_7$— | $n_D^{17}$ 1.5257 |
| 70 | " | " | i-C$_3$H$_7$— | $n_D^{17}$ 1.5196 |
| 71 | " | " | n-C$_4$H$_9$— | $n_D^{17}$ 1.5202 |
| 72 | " | " | i-C$_4$H$_9$— | $n_D^{17}$ 1.5180 |
| 73 | " | " | CH$_2$=CHCH$_2$— | $n_D^{17}$ 1.5431 |
| 74 | " | " | C$_2$H$_5$OCH$_2$CH$_2$— | $n_D^{17}$ 1.5195 |
| 75 | " | " | C$_6$H$_5$O—CH$_2$CH$_2$— | m.p. 66–69 |
| 76 | " | " | C$_6$H$_5$CH$_2$— | $n_D^{16}$ 1.5854 |
| 77 | " | " | C$_6$H$_5$CH$_2$CH$_2$— | $n_D^{16}$ 1.5610 |
| 78 | " | n-C$_4$H$_9$S— | CH$_3$— | $n_D^{11}$ 1.5393 |
| 79 | " | " | C$_2$H$_5$— | m.p. 42–43 |
| 80 | " | " | n-C$_3$H$_7$— | $n_D^{11}$ 1.5258 |
| 81 | " | " | i-C$_3$H$_7$— | $n_D^{11}$ 1.5142 |
| 82 | " | " | n-C$_4$H$_9$— | $n_D^{22}$ 1.5160 |
| 83 | " | " | i-C$_4$H$_9$— | $n_D^{22}$ 1.5129 |
| 84 | " | " | CH$_2$=CHCH$_2$— | $n_D^{22}$ 1.5365 |
| 85 | " | t-C$_4$H$_9$S— | C$_2$H$_5$— | m.p. 84–85 |
| 86 | " | " | n-C$_3$H$_7$— | $n_D^{22}$ 1.5196 |
| 87 | " | CH$_2$=CHCH$_2$S— | CH$_3$— | m.p. 74–75 |
| 88 | " | " | C$_2$H$_5$— | m.p. 61–63 |
| 89 | " | " | i-C$_3$H$_7$— | $n_D^{22}$ 1.5226 |
| 90 | " | CH$_3$OCH$_2$S— | C$_2$H$_5$— | $n_D^{27}$ 1.5268 |

TABLE 1a-continued

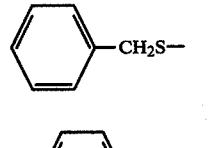

| Compound No. | R | $R_3$ | $R_2$ | Physicochemical data m.p. (°C.) or refractive index $n_D$ |
|---|---|---|---|---|
| 91 | " | 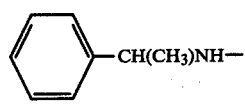 —CH$_2$S— | " | m.p. 57–58 |
| 92 | " | H$_3$C—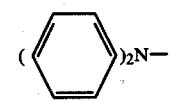—CH$_2$S— | CH$_3$— | m.p. 92–93 |
| 93 | " | " | n-C$_3$H$_7$— | $n_D^{22}$ 1.5697 |
| 94 | " | " | i-C$_3$H$_7$— | $n_D^{22}$ 1.5539 |
| 95 | " | " | n-C$_4$H$_9$— | $n_D^{22}$ 1.5538 |
| 96 | " | " | i-C$_4$H$_9$— | $n_D^{22}$ 1.5509 |
| 97 | " | " | CH$_2$=CHCH$_2$— | $n_D^{22}$ 1.5764 |
| 98 | " | CH$_3$NH— | CH$_3$ | m.p. 127–130 |
| 99 | " | " | C$_2$H$_5$— | m.p. 120–122 |
| 100 | " | C$_2$H$_5$NH— | " | m.p. 199–121 |
| 101 | " | n-C$_3$H$_7$NH— | CH$_3$— | m.p. 101–103 |
| 102 | " | " | C$_2$H$_5$— | m.p. 101–102 |
| 103 | " | " | n-C$_3$H$_7$— | m.p. 77–79 |
| 104 | " | " | i-C$_3$H$_7$— | m.p. 78–80 |
| 105 | CH$_3$— | " | n-C$_4$H$_9$— | m.p. 80–82 |
| 106 | " | " | i-C$_4$H$_9$— | m.p. 70–71 |
| 107 | " | " | CH$_2$=CHCH$_2$— | m.p. 75–77 |
| 108 | " | n-C$_4$H$_9$NH— | CH$_3$— | m.p. 111–113 |
| 109 | " | " | C$_2$H$_5$— | m.p. 88–90 |
| 110 | " | " | n-C$_3$H$_7$— | m.p. 65–67 |
| 111 | " | " | i-C$_3$H$_7$— | m.p. 59–61 |
| 112 | " | " | n-C$_4$H$_9$— | m.p. 77–78 |
| 113 | " | " | i-C$_4$H$_9$— | m.p. 64–66 |
| 114 | " | " | CH$_2$CH=CH— | m.p. 70–72 |
| 115 | " | (CH$_3$)$_2$N— | CH$_3$— | m.p. 121–122 |
| 116 | " | " | C$_2$H$_5$— | m.p. 75 |
| 117 | " | " | n-C$_3$H$_7$— | $n_D^{22}$ 1.5180 |
| 118 | " | " | i-C$_3$H$_7$— | $n_D^{22}$ 1.5109 |
| 119 | " | " | n-C$_4$H$_9$— | $n_D^{22}$ 1.5119 |
| 120 | " | " | i-C$_4$H$_9$— | $n_D^{22}$ 1.5120 |
| 121 | " | " | CH$_2$CH=CH$_2$— | $n_D^{22}$ 1.5356 |
| 122 | " | (C$_2$H$_5$)$_2$N— | CH$_3$— | $n_D^{21}$ 1.5267 |
| 123 | " | " | C$_2$H$_5$— | m.p. 54–55 |
| 124 | " | " | n-C$_3$H$_7$— | $n_D^{22}$ 1.5106 |
| 125 | " | " | i-C$_3$H$_7$— | $n_D^{22}$ 1.5051 |
| 126 | " | " | n-C$_4$H$_9$— | $n_D^{22}$ 1.5065 |
| 127 | " | " | i-C$_4$H$_9$— | $n_D^{22}$ 1.5046 |
| 128 | " | " | CH$_2$=CHCH$_2$— | $n_D^{22}$ 1.5270 |
| 129 | " | (n-C$_3$H$_7$)$_2$N— | CH$_3$— | $n_D^{21}$ 1.5186 |
| 130 | " | " | C$_2$H$_5$— | $n_D^{25}$ 1.5074 |
| 131 | " | " | n-C$_3$H$_7$— | $n_D^{23}$ 1.5070 |
| 132 | " | " | i-C$_3$H$_7$— | $n_D^{23}$ 1.5018 |
| 133 | " | " | n-C$_4$H$_9$— | $n_D^{23}$ 1.5043 |
| 134 | " | (n-C$_4$H$_9$)$_2$N— | CH$_3$— | $n_D^{21}$ 1.5137 |
| 135 | " | " | C$_2$H$_5$— | $n_D^{25}$ 1.5030 |
| 136 | " | " | n-C$_3$H$_7$— | $n_D^{23}$ 1.4971 |
| 137 | " | " | i-C$_3$H$_7$— | $n_D^{23}$ 1.4972 |
| 138 | " | " | n-C$_4$H$_9$— | $n_D^{23}$ 1.5002 |
| 139 | " | ⌬—CH(CH$_3$)NH— | C$_2$H$_5$— | m.p. 72–74 |
| 140 | " | (⌬)$_2$N— | CH$_3$— | m.p. 116–118 |

TABLE 1a-continued

Structure:

$$\begin{array}{c}\text{R}_2\text{OC}\underset{\text{O}}{\overset{\text{R}}{\underset{\|}{-}}}\text{S}\underset{\text{O}}{\overset{\text{OC}-\text{R}_3}{\underset{\|}{-}}}\text{COR}_2\end{array}$$

| Compound No. | R | R₃ | R₂ | Physicochemical data m.p. (°C.) or refractive index $n_D$ |
|---|---|---|---|---|
| 141 | " | " | $C_2H_5$ | m.p. 115–116 |
| 142 | " | " | $CH_3-$ | m.p. 110–111 |
|  |  | (cyclopentyl)H—NH— |  |  |
| 143 | " | " | $C_2H_5-$ | m.p. 119–121 |
| 144 | " | " | $n\text{-}C_3H_7-$ | m.p. 75–77 |
| 145 | " | " | $i\text{-}C_3H_7-$ | m.p. 99–100 |
| 146 | " | " | $n\text{-}C_4H_9-$ | m.p. 89–91 |
| 147 | " | " | $i\text{-}C_4H_9-$ | m.p. 86–88 |
| 148 | " | " | $sec\text{-}C_4H_9-$ | m.p. 67–68 |
| 149 | " | " | $CH_2=CHCH_2-$ | m.p. 88–90 |
| 150 | " | " | (phenyl)-$CH_2-$ | m.p. 140–142 |
| 151 | " | " | (phenyl)-$CH_2CH_2-$ | m.p. 70–72 |
| 152 | " | " | $C_2H_5OCH_2CH_2-$ | m.p. 73–75 |
| 153 | " | " | (phenyl)-$O-CH_2CH_2-$ | m.p. 116–118 |
| 154 | " | (cyclohexyl)H—NH— | $CH_3-$ | m.p. 140–141 |
| 155 | " | " | $C_2H_5-$ | m.p. 130–132 |
| 156 | " | " | $i\text{-}C_3H_7-$ | m.p. 96–97 |
| 157 | " | " | $n\text{-}C_4H_9-$ | m.p. 94–96 |
| 158 | " | " | $i\text{-}C_4H_9-$ | m.p. 82–83 |
| 159 | " | " | $CH_2=CHCH_2-$ | m.p. 93–94 |
| 160 | " | " | $CH\equiv CCH_2-$ | m.p. 145–147 |
| 161 | " | " | $sec\text{-}C_4H_9-$ | m.p. 79–81 |
| 162 | " | " | $n\text{-}C_8H_{17}-$ | m.p. 63–65 |
| 163 | " | " | (phenyl)-$CH_2-$ | m.p. 140–142 |
| 164 | " | " | (phenyl)-$CH_2CH_2-$ | m.p. 97–99 |
| 165 | " | " | $C_2H_5OCH_2CH_2-$ | m.p. 86–87 |
| 166 | " | " | (phenyl)-$O-CH_2CH_2-$ | m.p. 120–122 |
| 167 | " | " | $n\text{-}C_3H_7-$ | m.p. 90–94 |
| 168 | " | (cyclooctyl)—NH— | $C_2H_5-$ | m.p. 87–89 |
| 169 | " | " | $i\text{-}C_3H_7-$ | m.p. 63–65 |

TABLE 1a-continued

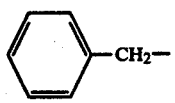

| Compound No. | R | R$_3$ | R$_2$ | Physicochemical data m.p. (°C.) or refractive index n$_D$ |
|---|---|---|---|---|
| 170 | " | (CH$_2$)$_4$N— | CH$_3$— | m.p. 112–115 |
| 171 | " | " | C$_2$H$_5$— | m.p. 110–111 |
| 172 | " | " | n-C$_3$H$_7$— | n$_D^{26}$ 1.5255 |
| 173 | " | " | i-C$_3$H$_7$— | m.p. 70–73 |
| 174 | " | " | n-C$_4$H$_9$— | n$_D^{26}$ 1.5199 |
| 175 | " | " | i-C$_4$H$_9$— | n$_D^{26}$ 1.5174 |
| 176 | " | " | CH$_2$=CHCH$_2$— | m.p. 62–65 |
| 177 | " | " | C$_2$H$_5$OCH$_2$CH$_2$— | n$_D^{26}$ 1.5189 |
| 178 | " | " |  —CH$_2$— | m.p. 104–105 |
| 179 | " | (CH$_2$)$_5$N— | CH$_3$— | m.p. 91–94 |
| 180 | " | " | C$_2$H$_5$— | m.p. 88–89 |
| 181 | " | " | n-C$_3$H$_7$— | n$_D^{26}$ 1.5222 |
| 182 | " | " | i-C$_3$H$_7$— | m.p. 66–69 |
| 183 | " | " | n-C$_4$H$_9$— | n$_D^{26}$ 1.5172 |
| 184 | " | " | i-C$_4$H$_9$— | n$_D^{26}$ 1.5158 |
| 185 | " | " | CH$_2$=CHCH$_2$— | n$_D^{26}$ 1.5389 |
| 186 | " | " | 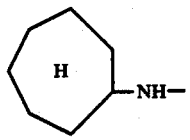 | m.p. 125–127 |
| 187 | " | i-C$_3$H$_7$NH— | C$_2$H$_5$— | m.p. 90–92 |
| 188 | " | " | n-Bu— | m.p. 70–72 |
| 189 | " | CH$_3$— | CH$_3$— | m.p. 119–120 |
| 190 | " | " | n-C$_3$H$_7$— | n$_D^{10}$ 1.5148 |
| 191 | " | " | i-C$_3$H$_7$— | n$_D^{21}$ 1.4976 |
| 192 | " | C$_2$H$_5$— | CH$_3$— | m.p. 71–72 |
| 193 | " | " | C$_2$H$_5$— | m.p. 53–55 |
| 194 | " | " | n-C$_3$H$_9$— | n$_D^{10}$ 1.5118 |
| 195 | " | " | i-C$_3$H$_7$— | n$_D^{22}$ 1.4943 |
| 196 | " | n-C$_3$H$_7$— | C$_2$H$_5$— | n$_D^{25}$ 1.5072 |
| 197 | " | n-C$_4$H$_9$— | n-C$_3$H$_7$— | n$_D^{11}$ 1.5258 |
| 198 | " | t-C$_4$H$_9$— | n-C$_3$H$_7$— | n$_D^{28}$ 1.5027 |
| 199 | " | i-C$_4$H$_9$— | " | n$_D^{27}$ 1.4971 |
| 200 | " | CH$_2$Cl— | " | m.p. 52–54 |
| 201 | " | CH$_2$Br— | " | m.p. 81–83 |
| 202 | " | CH$_3$CHCl— | " | m.p. 43–45 |
| 203 | " | CH$_3$CHBr— | n-C$_3$H$_7$— | m.p. 64–66 |
| 204 | " | CH$_3$CH$_2$CH$_2$CHBr— | " | n$_D^{23}$ 1.5130 |
| 205 | " | CH$_2$=CH— | CH$_3$— | m.p. 67–69 |
| 206 | " | " | C$_2$H$_5$— | n$_D^{25}$ 1.5031 |
| 207 | " | " | n-C$_3$H$_7$— | n$_D^{11}$ 1.5251 |
| 208 | " | " | i-C$_3$H$_7$— | n$_D^{11}$ 1.5107 |
| 209 | " | " | n-C$_4$H$_9$— | n$_D^{22}$ 1.5133 |
| 210 | " | " | i-C$_4$H$_9$— | n$_D^{22}$ 1.5086 |
| 211 | " | " | CH$_2$=CHCH$_2$— | n$_D^{22}$ 1.5352 |
| 212 | " | CH$_3$CH=CH— | C$_2$H$_5$— | n$_D^{27}$ 1.5244 |
| 213 | " | " | n-C$_3$H$_7$— | n$_D^{10}$ 1.5270 |
| 214 | " | " | i-C$_3$H$_7$— | n$_D^{20}$ 1.5115 |
| 215 | " | " | n-C$_4$H$_9$— | n$_D^{27}$ 1.5152 |
| 216 | " | " | i-C$_4$H$_9$— | n$_D^{27}$ 1.5110 |
| 217 | " | " | CH$_2$=CH—CH— | m.p. 76–48 |
| 218 | " | C$_2$H$_5$CH=CH— | CH$_3$— | m.p. 92–94 |

TABLE 1a-continued $$\text{structure: thiophene ring with } R_2OC(O)\text{-} \text{ and } \text{-}COR_2 \text{ at 2,5-positions, } R \text{ and } OC(O)R_3 \text{ at 3,4-positions}$$

| Compound No. | R | $R_3$ | $R_2$ | Physicochemical data m.p. (°C.) or refractive index $n_D$ |
|---|---|---|---|---|
| 219 | " | $(CH_3)_2C=CH-$ | $C_2H_5-$ | m.p. 77–78 |
| 220 | " | " | $CH_3-$ | m.p. 95–96 |
| 221 | " | " | $n\text{-}C_3H_7-$ | $n_D^{24}$ 1.5222 |
| 222 | " | " | $i\text{-}C_3H_7-$ | $n_D^{20}$ 1.5190 |
| 223 | " | " | $n\text{-}C_4H_9-$ | $n_D^{26}$ 1.5177 |
| 224 | " | " | $i\text{-}C_4H_9-$ | $n_D^{26}$ 1.5130 |
| 225 | " | " | $CH_2=CHCH_2-$ | m.p. 57–60 |
| 226 | " | $CH_3OCH_2-$ | $CH_3-$ | m.p. 81–83 |
| 227 | " | " | $C_2H_5-$ | $n_D^{10}$ 1.5125 |
| 228 | " | " | $n\text{-}C_3H_7-$ | $n_D^{10}$ 1.5125 |
| 229 | " | " | $i\text{-}C_3H_7-$ | $n_D^{22}$ 1.4971 |
| 230 | " | " | $n\text{-}C_4H_9-$ | $n_D^{23}$ 1.5037 |
| 231 | " | " | $CH_2=CHCH_2-$ | $n_D^{23}$ 1.5258 |
| 232 | " | $C_2H_5OCH_2-$ | $C_2H_5-$ | $n_D^{25}$ 1.5037 |
| 233 | " | $C_2H_5OC_2H_4-$ | $CH_3-$ | $n_D^{24}$ 1.5048 |
| 234 | " | " | $C_2H_5-$ | $n_D^{28}$ 1.4948 |
| 235 | " | " | $n\text{-}C_3H_7-$ | $n_D^{10}$ 1.5061 |
| 236 | " | " | $i\text{-}C_3H_7-$ | $n_D^{23}$ 1.4937 |
| 237 | " | " | $n\text{-}C_4H_9-$ | $n_D^{24}$ 1.4979 |
| 238 | " | " | $i\text{-}C_4H_9-$ | $n_D^{24}$ 1.4913 |
| 239 | " | " | $CH_2=CHCH_2-$ | $n_D^{24}$ 1.5170 |
| 240 | " | $CH_3CH(O\text{-}C_6H_4\text{-})-$ | $C_2H_5-$ | $n_D^{15}$ 1.5339 |
| 241 | " | $CH_3SCH_2-$ | " | m.p. 53–55 |
| 242 | " | $i\text{-}C_3H_7SCH_2-$ | " | $n_D^{25}$ 1.5261 |
| 243 | " | $CH_3OC(O)CH_2-$ | " | $n_D^{26}$ 1.5049 |
| 244 | " | $C_2H_5OC(O)CH_2-$ | " | $n_D^{26}$ 1.5037 |
| 245 | " | $C_6H_5CH=CH-$ | $n\text{-}C_4H_9-$ | $n_D^{15}$ 1.5615 |
| 246 | " | $CH_3OCH_2-$ | $i\text{-}C_4H_7-$ | $n_D^{23}$ 1.4996 |
| 247 | " | cyclopropyl | $C_2H_5-$ | $n_D^{26}$ 1.5163 |
| 248 | " | cyclohexyl (H) | " | m.p. 77–79 |
| 249 | " | " | $n\text{-}C_3H_7-$ | m.p. 40–41 |
| 250 | " | " | $i\text{-}C_3H_7-$ | $n_D^{17}$ 1.5132 |
| 251 | " | " | $n\text{-}C_4H_9-$ | $n_D^{17}$ 1.5148 |
| 252 | " | " | $i\text{-}C_4H_9-$ | $n_D^{17}$ 1.5124 |
| 253 | " | 2-thienyl | $CH_3-$ | m.p. 121–123 |
| 254 | " | " | $C_2H_5-$ | $n_D^{27}$ 1.5751 |
| 255 | " | " | $n\text{-}C_3H_7-$ | $n_D^{11}$ 1.5689 |
| 256 | " | " | $i\text{-}C_3H_7-$ | $n_D^{11}$ 1.5508 |

TABLE 1a-continued

[Structure: thiophene ring with R at one position, OC(=O)R₃ at adjacent, R₂OC(=O) and COR₂ groups]

| Compound No. | R | R₃ | R₂ | Physicochemical data m.p. (°C.) or refractive index $n_D$ |
|---|---|---|---|---|
| 257 | " | [furan-2-yl] | $C_2H_5$— | $n_D^{27}$ 1.5450 |
| 258 | " | $CH_3O$— | $CH_3$— | m.p. 80–81 |
| 259 | " | " | $C_2H_5$— | $n_D^{20}$ 1.5065 |
| 260 | " | " | n-$C_3H_7$— | $n_D^{10}$ 1.5122 |
| 261 | " | " | i-$C_3H_7$— | $n_D^{21}$ 1.4944 |
| 262 | " | $C_2H_5O$— | $C_2H_5$— | m.p. 50–52 |
| 263 | " | i-$C_4H_9O$— | " | $n_D^{23.5}$ 1.4958 |
| 264 | " | n-$C_5H_{11}O$— | " | m.p. 47–48 |
| 265 | " | n-$C_7H_5O$— | " | $n_D^{21}$ 1.4941 |
| 266 | " | n-$C_8H_{17}O$— | " | $n_D^{21}$ 1.4928 |
| 267 | " | n-$C_9H_{19}O$— | " | $n_D^{21}$ 1.4923 |
| 268 | " | $CH_2BrCHBrCH_2O$— | " | $n_D^{29}$ 1.5376 |
| 269 | " | $CH\equiv CCH_2O$— | " | $n_D^{24}$ 1.5101 |
| 270 | " | [phenyl]-O— | $CH_3$— | m.p. 118–119 |
| 271 | " | " | $C_2H_5$— | m.p. 103–105 |
| 272 | " | " | n-$C_3H_7$— | m.p. 79–80 |
| 273 | " | " | i-$C_3H_7$— | m.p. 62–64 |
| 274 | " | " | n-$C_4H_9$— | $n_D^{24}$ 1.5282 |
| 275 | " | " | i-$C_4H_9$— | $n_D^{20}$ 1.5280 |
| 276 | " | [2-Br-phenyl]-O— | $C_2H_5$— | m.p. 95–97 |
| 277 | " | [2-OCH₃-phenyl]-O— | " | m.p. 93–95 |
| 278 | " | [4-(H₃CS)-2-CH₃-phenyl]-O— | " | m.p. 76–77 |
| 279 | " | [phenyl]-O— | $CH_2=CHCH_2$— | m.p. 92–93 |
| 280 | " | [3-Br-phenyl]- | i-$C_3H_7$— | $n_D^{26}$ 1.5685 |
| 281 | " | [3-F-phenyl]- | " | $n_D^{26}$ 1.5362 |

TABLE 1a-continued
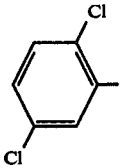
| Compound No. | R | R₃ | R₂ | Physicochemical data m.p. (°C.) or refractive index $n_D$ |
|---|---|---|---|---|
| 282 | " | 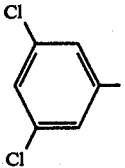 2,5-diCl-phenyl | " | $n_D^{26}$ 1.5744 |
| 283 | " | 3,5-diCl-phenyl | " | m.p. 130–133 |
| 284 | " | 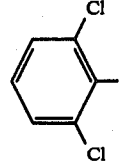 2,6-diCl-phenyl | " | m.p. 111–114 |
| 285 | " | 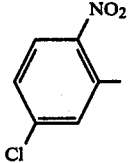 2-NO₂-4-Cl-phenyl | " | m.p. 130–132 |
| 286 | " | 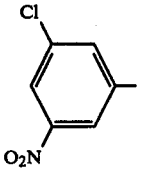 3-Cl-5-NO₂-phenyl | " | $n_D^{26}$ 1.5612 |
| 287 | " | 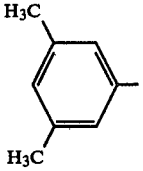 3,5-di-CH₃-phenyl | " | $n_D^{26}$ 1.5440 |
| 288 | " | 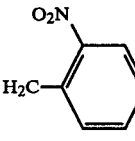 2-NO₂-4-CH₃-phenyl | " | m.p. 170–172 |

TABLE 1a-continued $$\text{structure with R, OC-R}_3\text{, R}_2\text{OC, S, COR}_2$$

| Compound No. | R | R₃ | R₂ | Physicochemical data m.p. (°C.) or refractive index $n_D$ |
|---|---|---|---|---|
| 289 | CH₃ | 2-CH₃-4-(O₂N)-C₆H₃– | " | m.p. 89–90 |
| 290 | " | 3-H₃CO-C₆H₄– | " | $n_D^{26}$ 1.5462 |
| 291 | " | 3,4-(H₃CO)₂-C₆H₃– | " | m.p. 114–115 |
| 292 | " | 2-NO₂-C₆H₄– | " | m.p. 124–126 |
| 293 | " | 4-NC-C₆H₄– | " | m.p. 89–91 |
| 294 | " | 3-NC-C₆H₄– | " | m.p. 137–139 |
| 295 | " | C₆H₅–CH₂– | " | $n_D^{23}$ 1.5404 |
| 296 | " | 4-Cl-C₆H₄–CH₂ | " | $n_D^{26}$ 1.5406 |
| 297 | " | 4-H₃CO-C₆H₄–CH₂ | " | $n_D^{26}$ 1.5426 |
| 298 | " | C₆H₅–CH₂CH₂– | " | $n_D^{26}$ 1.5327 |

TABLE 1a-continued
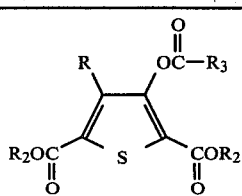
| Compound No. | R | $R_3$ | $R_2$ | Physicochemical data m.p. (°C.) or refractive index $n_D$ |
|---|---|---|---|---|
| 299 | " | 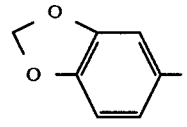 | " | $n_D^{27}$ 1.5609 |
| 300 | " | 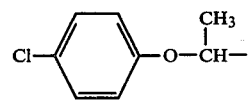 | " | $n_D^{26}$ 1.5324 |
| 301 | " | 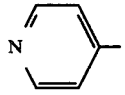 | " | $n_D^{26}$ 1.5378 |
| 302 | " | 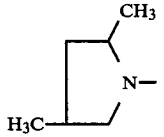 | " | m.p. 90–92 |
| 303 | " | 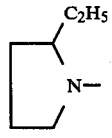 | " | $n_D^{18}$ 1.5173 |
| 304 | $CH_3$— | 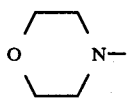 | " | $n_D^{18}$ 1.5173 |
| 305 | " | 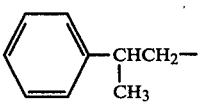 | " | $n_D^{18}$ 1.5192 |
| 306 | " |  | " | $n_D^{20}$ 1.5372 |

TABLE 1b $$\begin{array}{c} R \\ R_2-OC \\ \parallel \\ O \end{array} \begin{array}{c} O-S-R_4 \\ \parallel \\ O \end{array} \begin{array}{c} CO-R_2 \\ \parallel \\ O \end{array}$$

| Compound No. | R | R4 | R2 | Physico-chemical data m.p. (°C.) or refractive index $n_D$ |
|---|---|---|---|---|
| 307 | CH3— | CH3— | CH3— | m.p. 62-64° C. |
| 308 | " | " | C2H5— | m.p. 83-85° C. |
| 309 | " | " | n-C3H7— | $n_D^{19}$ 1.5200 |
| 310 | " | " | i-C3H7— | m.p. 95-96° C. |
| 311 | " | " | n-C4H9— | $n_D^{22}$ 1.5141 |
| 312 | " | " | i-C4H9— | $n_D^{22}$ 1.5106 |
| 313 | " | " | CH2=CHCH2— | $n_D^{22}$ 1.5397 |
| 314 | " | n-C3H7— | n-C4H9— | $n_D^{19}$ 1.5127 |
| 315 | " | " | i-C4H9— | $n_D^{19}$ 1.5049 |
| 316 | " | " | CH2=CHCH2— | $n_D^{20}$ 1.5302 |
| 317 | " | i-C3H7— | C2H5 | $n_D^{22}$ 1.5130 |
| 318 | " | n-C4H9— | CH3— | m.p. 51-54 |
| 319 | " | " | i-C3H7— | m.p. 59-61 |
| 320 | " | " | n-C4H9— | $n_D^{18}$ 1.5089 |
| 321 | " | " | i-C4H9— | $n_D^{18}$ 1.5022 |
| 322 | " | " | CH2=CHCH2— | $n_D^{18}$ 1.5293 |
| 323 | " | n-C5H11— | C2H5— | $n_D^{28}$ 1.5100 |
| 324 | " | (CH3)2N— | C2H5— | $n_D^{22}$ 1.5232 |
| 325 | " | ⟨phenyl⟩— | CH3— | m.p. 153-154 |
| 326 | " | " | i-C3H7— | $n_D^{19}$ 1.5437 |
| 327 | " | " | n-C4H9— | $n_D^{21}$ 1.5414 |
| 328 | " | " | i-C4H9— | $n_D^{21}$ 1.5359 |
| 329 | " | " | CH2=CHCH2— | $n_D^{21}$ 1.5667 |
| 330 | " | " | C2H5— | m.p. 90-91 |
| 331 | " | Cl—⟨phenyl⟩— | i-C3H7— | m.p. 99-101 |
| 332 | " | " | i-C4H9— | $n_D^{19}$ 1.5486 |
| 333 | " | " | CH2=CHCH2— | $n_D^{20}$ 1.5646 |
| 334 | " | Br—⟨phenyl⟩— | CH3— | m.p. 124-125 |
| 335 | " | " | C2H5— | m.p. 98-99 |
| 336 | " | " | n-C3H7— | m.p. 73-74 |
| 337 | " | " | i-C3H7— | m.p. 98-99 |
| 338 | " | " | n-C4H9— | $n_D^{22}$ 1.5530 |
| 339 | " | " | i-C4H9— | $n_D^{16}$ 1.5546 |
| 340 | " | H3C—⟨phenyl⟩— | CH3— | m.p. 115-117 |
| 341 | " | " | C2H5— | |
| 342 | " | " | n-C3H7— | m.p. 81-83 |
| 343 | " | " | i-C3H7— | m.p. 102-104 |
| 344 | " | " | n-C4H9— | $n_D^{20}$ 1.5374 |
| 345 | " | " | CH2=CHCH2— | m.p. 48-50 |
| 346 | " | i-C3H7— | CH3— | m.p. 143-145 |
| 347 | " | " | i-C3H7— | $n_D^{22}$ 1.5092 |

When the compounds of the present invention are used as agricultural and horticultural fungicides, they can be applied as they are or by diluting them with a liquid carrier such as water or an organic solvent or with a solid dust or other suitable carrier or by formulating them into wettable powder, oil, liquid, emulsion, sol (flowable), dust, driftless dust, granule and microgranule by adding auxiliary agents such as a wetting agent, a spreading agent, a dispersing agent, an emulsifying agent and a fixing agent as any occasion arises. As liquid carriers to be used for formulating, for example, solvents such as water, aromatic hydrocarbons, aliphatic hydrocarbons, alcohols, esters, ketones, acid amides and dimethylsulfoxide are usable. Solid carriers include mineral dusts such as clay, talc, kaolin, bentonite, diatomaceous earth, calcium carbonate and silicic acid. As auxiliary agents, for example, nonionic, anionic, cationic and amphoteric surfactants, lignin-sulfonic acid or its salts, gummy substances, aliphatic hydrocarbon salts, methyl cellulose and the like thickening agents are usable.

The formulations such as wettable powders, liquids, sols (flowable) and emulsions may contain their active components within the range of from 1 to 95% by weight, usually from 2 to 75% by weight.

These formulations are diluted with water to 0.0001% to 10% by weight in general and are applied at a rate of from 50 to 500 l per 10 ares, preferably from 100 to 300 l. Dusts, driftless dusts, microgranules and granules may contain in general 0.1 to 10% by weight of active components and are used at a rate of from 1 to 10 kg per 10 ares, preferably from 3 to 5 kg. Concentrated liquids such as oils, emulsions and sols (flowable) are usable as fine spray as they are without diluting them. Further, wettable powders and dusts are usable as seed dressings for crop seeds, and wettable powders, sols and emulsions when diluted with water are usable for immersing crop seeds.

In using the compounds of the present invention as agricultural and horticultural fungicides, it is possible to broaden their applicability by mixing them with insecticides, fungicides, herbicides and plant growth regulants. Depending on the situation, it is also possible to expect any synergistic effects.

Some examples are given below to illustrate the use as agricultural and horticultural fungicides of the compounds of the present invention, but it should not be construed that the principal ingredients and additives are not limited to those exemplified in these examples.

EXAMPLE 13

(Dust)

A homogeneous mixture of 2 parts of the compound No. 2 and 98 parts of clay is pulverized to obtain a dust preparation containing 2% of the effective ingredient.

EXAMPLE 14

(Wettable powder)

A homogeneous mixture of 30 parts of the compound No. 17, 3 parts of calcium alkylbenzenesulfonate, 5 parts of polyoxyethylene nonylphenyl ether and 62 parts of clay is pulverized uniformly to obtain a wettable powder containing 30% of the finely powdered effective ingredient. This wettable powder when actually applied to plants, is diluted to 1000 to 8000 times with water and then sprayed over the plants.

EXAMPLE 15

(Emulsion)

By dissolving 30 parts of the compound No. 4 in 55 parts of methyl ethyl ketone and 15 parts of polyethylene nonylphenyl ether, an emulsion containing 30% of the effective ingredient is obtained. The emulsion when actually applied to plants is diluted to 1000 to 8000 times with water and then sprayed over the plants.

EXAMPLE 16

(Granule)

A mixture of 5 parts of the compound No. 24, 1.5 parts of lauryl sulfate, 1.5 parts of calcium lignin-sulfonate, 25 parts of bentonite, 67 parts of acid clay and 15 parts of water is kneaded by means of a kneading machine, followed granulation. The granules thus obtained are then dried by means of a fluid bed type drier to obtain a granular preparation containing 5% of the effective ingredient.

EXAMPLE 17

(Dust)

A homogeneous mixture of 2 parts of the compound No. 32 and 98 parts of clay is uniformly pluverized to obtain a dust preparation containing 2% of the effective ingredient.

EXAMPLE 18

(Wettable powder)

A homogeneous mixture of 30 parts of the compound No. 36, 3 parts of calcium alkylbenzenesulfonate, 5 parts of polyoxyethylene nonylphenyl ether and 62 parts of clay is pulverized to obtain a wettable powder containing 3% of the effective ingredient. The wettable powder thus obtained when actually applied to plants is diluted to 1,000 to 8,000 times with water and then sprayed over the plants.

EXAMPLE 19

(Emulsion)

By dissolving 30 parts of the compound No. 45 in 55 parts of methyl ethyl ketone and 15 parts of polyoxyethylene nonylphenyl ether, an emulsion containing 30% of the effective ingredient is obtained. The emulsion thus obtained, when actually used, is diluted 1,000 to 8,000 times with water and then sprayed over the plants.

EXAMPLE 20

(Granule)

A mixture of 5 parts of the compound No. 62, 1.5 parts of lauryl sulfate, 1.5 parts of calcium lignin-sulfonate, 25 parts of bentonite, 67 parts of acid clay and 15 parts of water is kneaded by means of a kneading machine, followed by granulation. The granules thus obtained are then dried on a fluid bed type drier to obtain a granule preparation containing 5% of the effective ingredient.

EXAMPLE 21

(Dust)

A homogeneous mixture of 2 parts of the compound No. 69 and 98 parts of clay is uniformly pulverized to obtain a dust preparation containing 2% of the effective ingredient.

EXAMPLE 22

(Wettable powder)

A homogeneous mixture of 30 parts of the compound No. 73, 3 parts of calcium alkylbenzenesulfonate, 5 parts of polyoxyethylene nonylphenyl ether and 62 parts of clay is uniformly pulverized to obtain a wettable powder containing 3% of the effective ingredient. Thus obtained wettable powder when it is actually applied to plants is diluted to 1,000 to 8,000 times with water and then sprayed over the plants.

EXAMPLE 23

(Emulsion)

By dissolving 30 parts of the compound No. 92 in 55 parts of methyl ethyl ketone and 15 parts of polyoxyethylene nonylphenyl ether, an emulsion containing 30% of the effective ingredient is obtained. The emulsion thus obtained, when it is actually applied to plants, is diluted to 1,000 to 8,000 times with water and then sprayed over the plants.

EXAMPLE 24

(Granule)

A mixture of 5 parts of the compound No. 101, 1.5 parts of lauryl sulfate, 1.5 parts of calcium lignin-sulfonate, 25 parts of bentonite, 67 parts of clay and 15 parts of water is kneaded by means of a kneading machine, followed by granulation. The granules thus obtained are dried on a fluid bed type drier to obtain a granule preparation containing 5% of the effective ingredient.

EXAMPLE 25

(Dust)

A homogeneous mixture of 2 parts of the compound No. 109 and 98 parts of clay is uniformly pulverized to obtain a dust preparation containing 2% of the effective ingredient.

EXAMPLE 26

(Wettable powder)

A homogeneous mixture of 30 parts of the compound No. 124, 3 parts of calcium alkylbenzenesulfonate, 5 parts of polyoxyethylene nonylphenyl ether and 62 parts of clay is uniformly pulverized to obtain a wettable powder containing 3% of the effective ingredient. The wettable powder thus obtained, when it is actually applied to plants, is diluted to 1,000 to 8,000 times with water and then sprayed over the plants.

EXAMPLE 27

(Emulsion)

By dissolving 30 parts of compound No. 131 in 55 parts of methyl ethyl ketone and 15 parts of polyoxyethylene nonylphenyl ether, an emulsion containing 30% of the effective ingredient is obtained. The emulsion when actually applied to plants is diluted to 1,000 to 8,000 times with water and then sprayed over the plants.

EXAMPLE 28

(Granule)

A mixture of 5 parts of the compound No. 183, 1.5 parts of laryl sulfate, 1.5 parts of calcium lignin-sulfonate, 25 parts of bentonite, 67 parts of acid clay and 15 parts of water is kneaded by means of a kneading machine, followed by granulation. The granules thus obtained are dried on a fluid bed type drier to obtain a granule preparation containing 5% of the effective ingredient.

EXAMPLE 29

(Dust)

A homogeneous mixture of 2 parts of the compound No. 190 and 98 parts of clay is uniformly pulverized to obtain a dust preparation containing 2% of the effective ingredient.

EXAMPLE 30

(Wettable powder)

A homogeneous mixture of 30 parts of compound No. 204, 3 parts of calcium alkylbenzenesulfonate, 5 parts of polyoxyethylene nonylphenyl ether and 62 parts of clay is uniformly pulverized to obtain a wettable powder containing 3% of the effective ingredient. The wettable powder thus obtained, when it is actually applied to plants, is diluted to 1,000 to 8,000 times with water and then sprayed over the plants.

EXAMPLE 31

(Emulsion)

By dissolving 30 parts of the compound No. 256 in 55 parts of methyl ethyl ketone and 15 parts of polyoxyethylene nonylphenyl ether, an emulsion containing 30% of the effective ingredient is obtained. The emulsion thus obtained, when it is actually applied to plants, is diluted to 1,000 to 8,000 times with water and sprayed over the plants.

EXAMPLE 32

(Granule)

A mixture of 5 parts of the compound No. 274, 1.5 parts of lauryl sulfonate, 1.5 parts of calcium lignin-sulfonate, 25 parts of bentonite, 67 parts of acid clay and 15 parts of water is kneaded by means of a kneading machine, followed by granulation. The granules thus obtained are dried on a fluidized bed drier to obtain a granule preparation containing 5% of the effective ingredient.

EXAMPLE 33

(Dust)

A homogeneous mixture of 2 parts of the compound No. 304 and 98 parts of clay is uniformly pulverized to obtain a dust preparation containing 2% of the effective ingredient.

EXAMPLE 34

(Wettable powder)

A homogeneous mixture of 30 parts of the compound No. 308, 3 parts of calcium alkylbenzenesulfonate, 5 parts of polyoxyethylene nonylphenyl ether and 62 parts of clay is uniformly pulverized to obtain a wettable powder of the finely powdered uniform composition containing 30% of the effective ingredient. The wettable powder thus obtained, when it is actually applied to plants, is diluted to 1,000 to 8,000 times with water and then sprayed over the plants.

EXAMPLE 35

(Emulsion)

By dissolving 30 parts of the compound No. 306 in 55 parts of methyl ethyl ketone and 15 parts of polyethylene nonylphenyl ether, an emulsion containing 30% of the effective ingredient is obtained. The emulsion thus obtained, when it is actually applied to plants, is diluted to 1,000 to 8,000 times with water and sprayed over the plants.

EXAMPLE 36

(Granules)

A mixture of 5 parts of the compound No. 317, 1.5 parts of lauryl sulfate, 1.5 parts of calcium lignin-sulfonate, 25 parts of bentonite, 67 parts of acid clay and 15 parts of water is kneaded by means of a kneading machine, followed by granulation. The granules thus obtained are dried on a fluid bed type drier to obtain a granule preparation containing 5% of the effective ingredient.

Fungicidal activities of the compounds of the present invention are illustrated below with reference to test examples.

TEST EXAMPLE 1

Test for the control effect on paddy rice blast

Over the 3rd-leaf stage seedlings of paddy rice (variety: Asahi) soil-cultured in a biscuit pot of 9 cm in diameter in a greenhouse was sprayed a test liquid, which was prepared by diluting a wettable powder prepared according to the general procedure of Example 14 to a predetermined concentration, at an amount of 10 ml per each pot. One day after the spraying of test liquid, the seedlings were inoculated by atomization with a spore suspension of rice blast fungus (Pyricuralia oryzae). Upon completion of the inoculation, the seedlings were kept overnight under a wet house condition (at 95–100% relative humidity and 24°–25° C.). Five (5) days after the inoculation, the number of lesions per leaf of the third stage leaves was investigated and the control value (%) was calculated on the basis of the following expression. Furthermore, the phytotoxicity against the rice plant of the test compound was investigated according to a fixed numeral scale, the injury ratings of which are defined as mentioned below. The results obtained are as shown in Table 2.

$$\text{Control value (\%)} = \left(1 - \frac{\text{Average number of lesions per leaf in treated plot}}{\text{Average number of lesions per leaf in blank plot}}\right) \times 100$$

Injury rating:
5: Very severe phytotoxicity
4: Severe phytotoxicity
3: Great phytotoxicity
2: Moderate phytotoxicity
1: Slight phytotoxicity
0: No phytotoxicity

TABLE 2

(Paddy rice blast)

| Compound No. | Concentration of spray liquid (ppm) | Control value (%) | Degree of phytotoxicity |
|---|---|---|---|
| 1 | 100 | 100 | 0 |
| 2 | 100 | 82 | 0 |
| 4 | 100 | 88 | 0 |
| 8 | 100 | 86 | 0 |
| 9 | 100 | 100 | 0 |
| 11 | 100 | 98 | 0 |
| 16 | 100 | 97 | 0 |
| 23 | 100 | 100 | 0 |
| 98 | 200 | 100 | 0 |
|  | 100 | 80 | 0 |
| 108 | 200 | 100 | 0 |
|  | 100 | 100 | 0 |

TABLE 2-continued (Paddy rice blast)

| Compound No. | Concentration of spray liquid (ppm) | Control value (%) | Degree of phytotoxicity |
|---|---|---|---|
| 114 | 200 | 100 | 0 |
|  | 100 | 84 | 0 |
| 116 | 200 | 100 | 0 |
|  | 100 | 100 | 0 |
| 117 | 200 | 100 | 0 |
|  | 100 | 100 | 0 |
| 118 | 200 | 100 | 0 |
|  | 100 | 85 | 0 |
| 120 | 200 | 100 | 0 |
|  | 100 | 88 | 0 |
| 122 | 200 | 100 | 0 |
|  | 100 | 86 | 0 |
| 124 | 200 | 100 | 0 |
|  | 100 | 86 | 0 |
| 125 | 200 | 100 | 0 |
|  | 100 | 95 | 0 |
| 128 | 200 | 100 | 0 |
|  | 100 | 93 | 0 |
| 139 | 200 | 100 | 0 |
|  | 100 | 95 | 0 |
| 146 | 200 | 100 | 0 |
|  | 100 | 96 | 0 |
| 147 | 200 | 100 | 0 |
|  | 100 | 93 | 0 |
| 149 | 200 | 100 | 0 |
|  | 100 | 100 | 0 |
| 156 | 200 | 100 | 0 |
|  | 100 | 81 | 0 |
| 170 | 200 | 100 | 0 |
|  | 100 | 82 | 0 |
| 173 | 200 | 100 | 0 |
|  | 100 | 80 | 0 |
| 180 | 200 | 100 | 0 |
|  | 100 | 84 | 0 |
| 198 | 100 | 91 | 0 |
| 199 | 100 | 100 | 0 |
| 201 | 100 | 100 | 0 |
| 202 | 100 | 79 | 0 |
| 212 | 100 | 100 | 0 |
| 217 | 100 | 100 | 0 |
| 219 | 100 | 100 | 0 |
| 221 | 100 | 77 | 0 |
| 225 | 100 | 79 | 0 |
| 227 | 100 | 100 | 0 |
| 228 | 100 | 95 | 0 |
| 233 | 100 | 88 | 0 |
| 234 | 100 | 100 | 0 |
| 235 | 100 | 99 | 0 |
| 238 | 100 | 76 | 0 |
| 239 | 100 | 87 | 0 |
| 242 | 100 | 100 | 0 |
| 243 | 100 | 82 | 0 |
| 244 | 100 | 100 | 0 |
| 247 | 100 | 100 | 0 |
| 248 | 100 | 100 | 0 |
| 249 | 100 | 100 | 0 |
| 250 | 100 | 100 | 0 |
| 251 | 100 | 100 | 0 |
| 253 | 100 | 85 | 0 |
| 254 | 100 | 96 | 0 |
| 256 | 100 | 88 | 0 |
| 257 | 100 | 91 | 0 |
| 262 | 100 | 91 | 0 |
| 263 | 100 | 84 | 0 |
| 271 | 100 | 70 | 0 |
| 272 | 100 | 70 | 0 |
| 276 | 100 | 100 | 0 |
| 292 | 100 | 90 | 0 |
| 303 | 100 | 87 | 0 |
| 304 | 100 | 87 | 0 |
| 305 | 100 | 100 | 0 |
| 306 | 100 | 100 | 0 |
| 308 | 200 | 100 | 0 |
|  | 100 | 100 | 0 |
| 309 | 200 | 100 | 0 |
|  | 100 | 79 | 0 |
| 320 | 200 | 100 | 0 |
|  | 100 | 86 | 0 |
| 323 | 200 | 100 | 0 |
|  | 100 | 100 | 0 |
| 324 | 200 | 100 | 0 |
|  | 100 | 100 | 0 |
| 325 | 200 | 100 | 0 |
|  | 100 | 75 | 0 |
| 331 | 200 | 100 | 0 |
|  | 100 | 76 | 0 |
| 340 | 200 | 100 | 0 |
|  | 100 | 82 | 0 |
| 342 | 200 | 100 | 0 |
|  | 100 | 74 | 0 |
| 343 | 200 | 100 | 0 |
|  | 100 | 74 | 0 |
| 345 | 200 | 100 | 0 |
|  | 100 | 85 | 0 |
| Comparative chemical (EDDP) | 200 | 100 | 0 |
|  | 100 | 95 | 0 |
| Non-treated | — | 0 | — |

(Note)

EDDP:
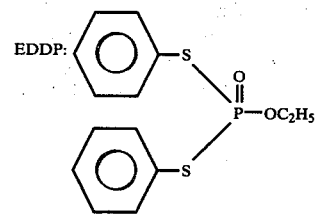

TEST EXAMPLE 2

Test for the control effect on cucumber powdery mildew

Over the first-leaf stage seedlings of cucumber (variety: Sagami hanjiro) soil-cultured in a porcelain pot of 9 cm in diatmeter in a greenhouse was sprayed 10 ml of a test solution of the compound diluted to a predetermined concentration. Next day the seedlings were inoculated by atomization with a spore suspension of cucumber powdery mildew fungus (Erysiphe cichobrcearum). Ten (10) days after the inoculation, percent lesion area (%) was investigated and the control value (%) was calculated according to the following expression.

$$\text{Preventive value (\%)} = \left(1 - \frac{\text{Percent lesion area in treated plot}}{\text{Percent lesion area in blank plot}}\right) \times 100$$

The results obtained are as shown in Table 3.

TABLE 3

(Cucumber powdery mildew)

| Compound No. | Concentration of spray liquid (ppm) | Control value (%) | Degree of phytotoxicity |
|---|---|---|---|
| 1 | 50 | 100 | 0 |
|  | 12.5 | 100 | 0 |
| 2 | 50 | 100 | 0 |
|  | 12.5 | 83 | 0 |
| 3 | 50 | 100 | 0 |
|  | 12.5 | 97 | 0 |
| 4 | 50 | 100 | 0 |
|  | 12.5 | 100 | 0 |

TABLE 3-continued

| Compound No. | Concentration of spray liquid (ppm) | Control value (%) | Degree of phytotoxicity |
|---|---|---|---|
| 5 | 50 | 100 | 0 |
|  | 12.5 | 81 | 0 |
| 6 | 50 | 100 | 0 |
|  | 12.5 | 92 | 0 |
| 7 | 50 | 100 | 0 |
|  | 12.5 | 79 | 0 |
| 8 | 50 | 100 | 0 |
|  | 12.5 | 100 | 0 |
| 9 | 50 | 100 | 0 |
|  | 12.5 | 58 | 0 |
| 10 | 50 | 100 | 0 |
|  | 12.5 | 70 | 0 |
| 11 | 50 | 95 | 0 |
|  | 12.5 | 64 | 0 |
| 12 | 50 | 86 | 0 |
|  | 12.5 | 62 | 0 |
| 13 | 50 | 100 | 0 |
|  | 12.5 | 80 | 0 |
| 14 | 50 | 100 | 0 |
|  | 12.5 | 100 | 0 |
| 15 | 50 | 100 | 0 |
|  | 12.5 | 50 | 0 |
| 16 | 50 | 100 | 0 |
|  | 12.5 | 100 | 0 |
| 17 | 50 | 100 | 0 |
|  | 12.5 | 100 | 0 |
| 18 | 50 | 100 | 0 |
|  | 12.5 | 84 | 0 |
| 19 | 50 | 100 | 0 |
|  | 12.5 | 98 | 0 |
| 20 | 50 | 100 | 0 |
|  | 12.5 | 54 | 0 |
| 21 | 50 | 100 | 0 |
|  | 12.5 | 92 | 0 |
| 22 | 50 | 80 | 0 |
|  | 12.5 | 34 | 0 |
| 23 | 50 | 100 | 0 |
|  | 12.5 | 52 | 0 |
| 24 | 50 | 100 | 0 |
|  | 12.5 | 100 | 0 |
| 25 | 50 | 100 | 0 |
|  | 12.5 | 73 | 0 |
| 26 | 50 | 85 | 0 |
|  | 12.5 | 62 | 0 |
| 27 | 50 | 65 | 0 |
|  | 12.5 | 43 | 0 |
| 28 | 50 | 100 | 0 |
|  | 12.5 | 100 | 0 |
| 29 | 50 | 100 | 0 |
|  | 12.5 | 68 | 0 |
| 30 | 50 | 100 | 0 |
|  | 12.5 | 100 | 0 |
| 31 | 50 | 100 | 0 |
|  | 12.5 | 98 | 0 |
| 32 | 50 | 100 | 0 |
|  | 12.5 | 100 | 0 |
| 33 | 50 | 100 | 0 |
|  | 12.5 | 100 | 0 |
| 34 | 50 | 100 | 0 |
|  | 12.5 | 100 | 0 |
| 35 | 50 | 100 | 0 |
|  | 12.5 | 90 | 0 |
| 36 | 50 | 100 | 0 |
|  | 12.5 | 90 | 0 |
| 37 | 50 | 100 | 0 |
|  | 12.5 | 100 | 0 |
| 38 | 50 | 100 | 0 |
|  | 12.5 | 82 | 0 |
| 39 | 50 | 100 | 0 |
|  | 12.5 | 100 | 0 |
| 40 | 50 | 100 | 0 |
|  | 12.5 | 100 | 0 |
| 41 | 50 | 100 | 0 |
| 42 | 50 | 100 | 0 |
| 43 | 50 | 90 | 0 |
| 44 | 50 | 100 | 0 |
|  | 12.5 | 91 | 0 |
| 45 | 50 | 100 | 0 |
| 46 | 50 | 100 | 0 |
|  | 12.5 | 90 | 0 |
| 47 | 50 | 100 | 0 |
|  | 12.5 | 100 | 0 |
| 48 | 50 | 100 | 0 |
|  | 12.5 | 100 | 0 |
| 49 | 50 | 100 | 0 |
|  | 12.5 | 100 | 0 |
| 50 | 50 | 100 | 0 |
| 51 | 50 | 100 | 0 |
|  | 12.5 | 100 | 0 |
| 52 | 50 | 82 | 0 |
| 53 | 50 | 100 | 0 |
|  | 12.5 | 100 | 0 |
| 54 | 50 | 86 | 0 |
| 55 | 50 | 100 | 0 |
| 56 | 50 | 100 | 0 |
| 57 | 50 | 74 | 0 |
| 58 | 50 | 100 | 0 |
|  | 12.5 | 100 | 0 |
| 59 | 50 | 100 | 0 |
|  | 12.5 | 100 | 0 |
| 60 | 50 | 100 | 0 |
|  | 12.5 | 80 | 0 |
| 61 | 50 | 100 | 0 |
| 62 | 50 | 100 | 0 |
|  | 12.5 | 100 | 0 |
| 63 | 50 | 100 | 0 |
|  | 12.5 | 100 | 0 |
| 64 | 50 | 100 | 0 |
|  | 12.5 | 100 | 0 |
| 65 | 50 | 100 | 0 |
|  | 12.5 | 100 | 0 |
| 66 | 50 | 100 | 0 |
|  | 12.5 | 80 | 0 |
| 67 | 50 | 100 | 0 |
|  | 12.5 | 85 | 0 |
| 68 | 50 | 100 | 0 |
|  | 25 | 100 | 0 |
| 69 | 50 | 100 | 0 |
|  | 12.5 | 100 | 0 |
| 70 | 50 | 100 | 0 |
|  | 12.5 | 100 | 0 |
| 71 | 50 | 100 | 0 |
|  | 12.5 | 100 | 0 |
| 72 | 50 | 100 | 0 |
|  | 25 | 100 | 0 |
| 73 | 50 | 100 | 0 |
|  | 25 | 93 | 0 |
| 74 | 50 | 100 | 0 |
| 75 | 50 | 100 | 0 |
|  | 25 | 83 | 0 |
| 76 | 50 | 100 | 0 |
|  | 25 | 87 | 0 |
| 77 | 100 | 100 | 0 |
|  | 50 | 75 | 0 |
| 78 | 100 | 95 | 0 |
|  | 50 | 75 | 0 |
| 79 | 50 | 100 | 0 |
|  | 25 | 100 | 0 |
| 80 | 50 | 100 | 0 |
|  | 12.5 | 100 | 0 |
| 81 | 50 | 100 | 0 |
|  | 12.5 | 100 | 0 |
| 82 | 50 | 100 | 0 |
|  | 12.5 | 100 | 0 |
| 83 | 50 | 100 | 0 |
|  | 25 | 100 | 0 |
| 84 | 50 | 100 | 0 |
|  | 12.5 | 100 | 0 |
| 85 | 50 | 100 | 0 |
|  | 12.5 | 100 | 0 |
| 86 | 50 | 100 | 0 |
|  | 12.5 | 100 | 0 |
| 87 | 100 | 90 | 0 |
|  | 50 | 75 | |

TABLE 3-continued

| Compound No. | (Cucumber powdery mildew) Concentration of spray liquid (ppm) | Control value (%) | Degree of phytotoxicity |
|---|---|---|---|
| 88 | 50 | 100 | 0 |
|  | 12.5 | 100 | 0 |
| 89 | 50 | 100 | 0 |
| 90 | 50 | 100 | 0 |
|  | 25 | 100 | 0 |
| 91 | 50 | 100 | 0 |
|  | 25 | 100 | 0 |
| 92 | 50 | 100 | 0 |
|  | 12.5 | 100 | 0 |
| 93 | 50 | 100 | 0 |
|  | 25 | 100 | 0 |
| 94 | 50 | 100 | 0 |
|  | 25 | 100 | 0 |
| 95 | 50 | 100 | 0 |
|  | 12.5 | 100 | 0 |
| 96 | 50 | 79 | 0 |
| 97 | 50 | 100 | 0 |
|  | 25 | 72 | 0 |
| 98 | 200 | 96 | 0 |
| 99 | 100 | 100 | 0 |
|  | 50 | 86 | 0 |
| 100 | 200 | 97 | 0 |
| 101 | 200 | 94 | 0 |
| 102 | 50 | 100 | 0 |
|  | 25 | 93 | 0 |
| 103 | 50 | 100 | 0 |
|  | 25 | 86 | 0 |
| 104 | 100 | 100 | 0 |
|  | 50 | 94 | 0 |
| 105 | 50 | 100 | 0 |
|  | 12.5 | 100 | 0 |
| 106 | 50 | 100 | 0 |
|  | 25 | 100 | 0 |
| 107 | 100 | 100 | 0 |
|  | 50 | 80 | 0 |
| 108 | 200 | 100 | 0 |
| 109 | 50 | 100 | 0 |
|  | 12.5 | 90 | 0 |
| 110 | 50 | 100 | 0 |
|  | 25 | 100 | 0 |
| 111 | 50 | 100 | 0 |
|  | 25 | 100 | 0 |
|  | 12.5 | 82 | 0 |
| 112 | 50 | 100 | 0 |
|  | 12.5 | 100 | 0 |
| 113 | 50 | 100 | 0 |
|  | 25 | 100 | 0 |
|  | 12.5 | 86 | 0 |
| 114 | 50 | 100 | 0 |
|  | 25 | 100 | 0 |
| 115 | 200 | 100 | 0 |
|  | 100 | 95 | 0 |
| 116 | 200 | 96 | 0 |
| 117 | 100 | 100 | 0 |
| 118 | 100 | 100 | 0 |
|  | 50 | 95 | 0 |
|  | 12.5 | 97 | 0 |
| 119 | 100 | 100 | 0 |
| 120 | 100 | 95 | 0 |
| 121 | 100 | 100 | 0 |
|  | 50 | 100 | 0 |
| 122 | 200 | 93 | 0 |
| 123 | 100 | 100 | 0 |
|  | 50 | 100 | 0 |
|  | 12.5 | 100 | 0 |
| 124 | 50 | 100 | 0 |
|  | 12.5 | 100 | 0 |
| 125 | 50 | 100 | 0 |
|  | 12.5 | 100 | 0 |
| 126 | 50 | 100 | 0 |
|  | 12.5 | 100 | 0 |
| 127 | 100 | 100 | 0 |
|  | 50 | 100 | 0 |
|  | 25 | 90 | 0 |
| 128 | 50 | 100 | 0 |
|  | 12.5 | 100 | 0 |
| 129 | 100 | 100 | 0 |
| 130 | 50 | 100 | 0 |
|  | 12.5 | 100 | 0 |
| 131 | 50 | 100 | 0 |
|  | 12.5 | 100 | 0 |
| 132 | 50 | 100 | 0 |
|  | 12.5 | 100 | 0 |
| 133 | 50 | 100 | 0 |
|  | 12.5 | 100 | 0 |
| 134 | 100 | 100 | 0 |
|  | 50 | 96 | 0 |
| 135 | 50 | 100 | 0 |
|  | 12.5 | 100 | 0 |
| 136 | 50 | 100 | 0 |
|  | 12.5 | 100 | 0 |
| 137 | 50 | 100 |  |
|  | 25 | 90 |  |
| 138 | 50 | 100 | 0 |
|  | 25 | 100 | 0 |
|  | 12.5 | 93 | 0 |
| 139 | 50 | 100 | 0 |
|  | 12.5 | 86 | 0 |
| 140 | 100 | 100 | 0 |
|  | 50 | 90 | 0 |
| 141 | 200 | 96 | 0 |
| 142 | 200 | 100 | 0 |
| 143 | 100 | 100 | 0 |
|  | 50 | 100 | 0 |
| 144 | 100 | 100 | 0 |
|  | 50 | 100 | 0 |
| 145 | 100 | 100 | 0 |
|  | 50 | 100 | 0 |
| 146 | 50 | 100 | 0 |
|  | 12.5 | 100 | 0 |
| 147 | 100 | 100 | 0 |
|  | 50 | 100 | 0 |
| 148 | 100 | 100 | 0 |
|  | 50 | 100 | 0 |
|  | 25 | 94 | 0 |
| 149 | 50 | 100 | 0 |
|  | 25 | 100 | 0 |
| 150 | 200 | 100 | 0 |
|  | 100 | 100 | 0 |
|  | 50 | 94 | 0 |
| 151 | 200 | 100 | 0 |
|  | 100 | 100 | 0 |
|  | 50 | 95 | 0 |
| 152 | 200 | 96 | 0 |
| 153 | 200 | 100 | 0 |
| 154 | 200 | 95 | 0 |
| 155 | 50 | 100 | 0 |
|  | 12.5 | 100 | 0 |
| 156 | 50 | 100 | 0 |
|  | 12.5 | 100 | 0 |
| 157 | 50 | 100 | 0 |
|  | 12.5 | 100 | 0 |
| 158 | 50 | 100 | 0 |
|  | 12.5 | 100 | 0 |
| 159 | 50 | 100 | 0 |
|  | 12.5 | 100 | 0 |
| 160 | 200 | 100 | 0 |
|  | 100 | 95 | 0 |
| 161 | 100 | 100 | 0 |
|  | 50 | 100 | 0 |
| 162 | 200 | 94 | 0 |
| 163 | 100 | 100 | 0 |
|  | 50 | 92 | 0 |
| 164 | 200 | 100 | 0 |
|  | 100 | 100 | 0 |
| 165 | 100 | 100 | 0 |
| 166 | 200 | 97 | 0 |
| 167 | 50 | 100 | 0 |
|  | 12.5 | 100 | 0 |
| 168 | 50 | 100 | 0 |
|  | 25 | 95 | 0 |
| 169 | 50 | 100 | 0 |
|  | 12.5 | 82 | 0 |
| 170 | 200 | 97 | 0 |

TABLE 3-continued (Cucumber powdery mildew)

| Compound No. | Concentration of spray liquid (ppm) | Control value (%) | Degree of phytotoxicity |
|---|---|---|---|
| 171 | 50 | 100 | 0 |
|  | 12.5 | 100 | 0 |
| 172 | 100 | 100 | 0 |
|  | 50 | 100 | 0 |
| 173 | 100 | 100 | 0 |
|  | 50 | 100 | 0 |
| 174 | 100 | 100 | 0 |
|  | 50 | 100 | 0 |
| 175 | 100 | 100 | 0 |
| 176 | 200 | 100 | 0 |
|  | 100 | 100 | 0 |
| 177 | 200 | 100 | 0 |
| 178 | 200 | 100 | 0 |
|  | 100 | 100 | 0 |
| 179 | 200 | 100 | 0 |
| 180 | 100 | 100 | 0 |
|  | 50 | 100 | 0 |
| 181 | 50 | 100 | 0 |
|  | 25 | 90 | 0 |
|  | 12.5 | 82 | 0 |
| 182 | 50 | 100 | 0 |
|  | 12.5 | 94 | 0 |
| 183 | 50 | 100 | 0 |
|  | 12.5 | 100 | 0 |
| 184 | 100 | 100 | 0 |
|  | 50 | 100 | 0 |
| 185 | 50 | 100 | 0 |
|  | 25 | 90 | 0 |
| 186 | 100 | 100 | 0 |
|  | 50 | 100 | 0 |
|  | 12.5 | 100 | 0 |
| 187 | 50 | 100 | 0 |
|  | 12.5 | 100 | 0 |
| 188 | 50 | 100 | 0 |
|  | 25 | 91 | 0 |
| 189 | 200 | 100 | 0 |
| 190 | 200 | 100 | 0 |
| 191 | 200 | 100 | 0 |
| 192 | 200 | 100 | 0 |
| 193 | 100 | 100 | 0 |
|  | 50 | 91 | 0 |
| 194 | 200 | 100 | 0 |
| 195 | 200 | 100 | 0 |
| 196 | 100 | 100 | 0 |
|  | 50 | 88 | 0 |
| 197 | 50 | 100 | 0 |
|  | 12.5 | 100 | 0 |
| 198 | 100 | 100 | 0 |
|  | 50 | 73 | 0 |
| 199 | 100 | 100 | 0 |
|  | 50 | 96 | 0 |
| 200 | 200 | 100 | 0 |
|  | 100 | 78 | 0 |
| 201 | 200 | 100 | 0 |
|  | 100 | 83 | 0 |
| 202 | 200 | 100 | 0 |
|  | 100 | 95 | 0 |
| 203 | 100 | 100 | 0 |
|  | 50 | 90 | 0 |
| 204 | 100 | 100 | 0 |
|  | 50 | 93 | 0 |
| 205 | 200 | 100 | 0 |
| 206 | 200 | 100 | 0 |
|  | 100 | 91 | 0 |
| 207 | 200 | 100 | 0 |
| 208 | 200 | 100 | 0 |
| 209 | 200 | 100 | 0 |
| 210 | 200 | 100 | 0 |
|  | 100 | 90 | 0 |
| 211 | 200 | 100 | 0 |
| 212 | 100 | 100 | 0 |
|  | 50 | 93 | 0 |
| 213 | 100 | 100 | 0 |
|  | 50 | 82 | 0 |
|  | 12.5 | 70 | 0 |
| 214 | 100 | 100 | 0 |
|  | 50 | 90 | 0 |
| 215 | 50 | 100 | 0 |
|  | 12.5 | 84 | 0 |
| 216 | 50 | 100 | 0 |
| 217 | 100 | 100 | 0 |
|  | 50 | 96 | 0 |
| 218 | 200 | 100 | 0 |
| 219 | 50 | 100 | 0 |
|  | 12.5 | 100 | 0 |
| 220 | 200 | 100 | 0 |
|  | 100 | 95 | 0 |
| 221 | 50 | 100 | 0 |
|  | 12.5 | 100 | 0 |
| 222 | 100 | 100 | 0 |
|  | 50 | 80 | 0 |
| 223 | 50 | 100 | 0 |
|  | 12.5 | 100 | 0 |
| 224 | 100 | 100 | 0 |
|  | 50 | 83 | 0 |
| 225 | 50 | 100 | 0 |
|  | 12.5 | 90 | 0 |
| 226 | 200 | 100 | 0 |
| 227 | 200 | 100 | 0 |
| 228 | 200 | 100 | 0 |
| 229 | 200 | 100 | 0 |
| 230 | 200 | 100 | 0 |
| 231 | 100 | 100 | 0 |
|  | 50 | 93 | 0 |
|  | 12.5 | 78 | 0 |
| 232 | 100 | 100 | 0 |
|  | 50 | 87 | 0 |
| 233 | 200 | 100 | 0 |
| 234 | 100 | 100 | 0 |
|  | 50 | 75 | 0 |
| 235 | 200 | 100 | 0 |
|  | 100 | 91 | 0 |
| 236 | 200 | 100 | 0 |
|  | 100 | 77 | 0 |
| 237 | 50 | 100 | 0 |
|  | 12.5 | 85 | 0 |
| 238 | 100 | 100 | 0 |
|  | 50 | 89 | 0 |
| 239 | 100 | 100 | 0 |
|  | 50 | 84 | 0 |
| 240 | 200 | 100 | 0 |
| 241 | 200 | 100 | 0 |
|  | 100 | 90 | 0 |
| 242 | 100 | 100 | 0 |
|  | 50 | 96 | 0 |
| 243 | 200 | 100 | 0 |
|  | 100 | 90 | 0 |
| 244 | 100 | 100 | 0 |
|  | 50 | 83 | 0 |
| 245 | 50 | 100 | 0 |
| 246 | 50 | 100 | 0 |
|  | 12.5 | 100 | 0 |
| 247 | 50 | 100 | 0 |
|  | 12.5 | 97 | 0 |
| 248 | 50 | 100 | 0 |
|  | 12.5 | 70 | 0 |
| 249 | 50 | 100 | 0 |
|  | 12.5 | 88 | 0 |
| 250 | 50 | 100 | 0 |
|  | 12.5 | 80 | 0 |
| 251 | 50 | 100 | 0 |
|  | 12.5 | 100 | 0 |
| 252 | 50 | 100 | 0 |
|  | 12.5 | 70 | 0 |
| 253 | 100 | 100 | 0 |
|  | 50 | 86 | 0 |
| 254 | 50 | 100 | 0 |
|  | 12.5 | 100 | 0 |
| 255 | 50 | 100 | 0 |
|  | 12.5 | 100 | 0 |
| 256 | 50 | 100 | 0 |
|  | 12.5 | 100 | 0 |
| 257 | 100 | 100 | 0 |
|  | 50 | 84 | 0 |

TABLE 3-continued (Cucumber powdery mildew)

| Compound No. | Concentration of spray liquid (ppm) | Control value (%) | Degree of phytotoxicity |
|---|---|---|---|
| 258 | 200 | 100 | 0 |
| 259 | 200 | 100 | 0 |
| 260 | 100 | 100 | 0 |
|  | 50 | 81 | 0 |
| 261 | 200 | 100 | 0 |
| 262 | 100 | 100 | 0 |
|  | 50 | 100 | 0 |
| 263 | 50 | 100 | 0 |
|  | 12.5 | 100 | 0 |
| 264 | 200 | 100 | 0 |
| 265 | 200 | 100 | 0 |
|  | 100 | 100 | 0 |
| 266 | 200 | 100 | 0 |
|  | 100 | 90 | 0 |
| 267 | 200 | 100 | 0 |
|  | 100 | 76 | 0 |
| 268 | 50 | 100 | 0 |
|  | 12.5 | 96 | 0 |
| 269 | 100 | 100 | 0 |
|  | 50 | 96 | 0 |
| 270 | 100 | 100 | 0 |
|  | 50 | 85 | 0 |
| 271 | 50 | 100 | 0 |
|  | 12.5 | 84 | 0 |
| 272 | 100 | 100 | 0 |
|  | 50 | 100 | 0 |
| 273 | 100 | 100 | 0 |
|  | 50 | 100 | 0 |
| 274 | 100 | 100 | 0 |
| 275 | 200 | 100 | 0 |
|  | 100 | 94 | 0 |
| 276 | 100 | 100 | 0 |
|  | 50 | 82 | 0 |
| 277 | 100 | 100 | 0 |
|  | 50 | 90 | 0 |
| 278 | 100 | 100 | 0 |
|  | 50 | 81 | 0 |
| 279 | 100 | 100 | 0 |
|  | 50 | 80 | 0 |
| 280 | 50 | 100 | 0 |
|  | 12.5 | 100 | 0 |
| 281 | 50 | 100 | 0 |
|  | 12.5 | 100 | 0 |
| 282 | 50 | 100 | 0 |
|  | 12.5 | 100 | 0 |
| 283 | 50 | 100 | 0 |
|  | 12.5 | 100 | 0 |
| 284 | 50 | 100 | 0 |
|  | 12.5 | 100 | 0 |
| 285 | 100 | 100 | 0 |
| 286 | 50 | 100 | 0 |
|  | 12.5 | 82 | 0 |
| 287 | 50 | 100 | 0 |
|  | 12.5 | 100 | 0 |
| 288 | 50 | 100 | 0 |
|  | 12.5 | 100 | 0 |
| 289 | 50 | 100 | 0 |
|  | 12.5 | 100 | 0 |
| 290 | 50 | 100 | 0 |
|  | 12.5 | 100 | 0 |
| 291 | 50 | 100 | 0 |
|  | 12.5 | 100 | 0 |
| 292 | 50 | 100 | 0 |
|  | 12.5 | 96 | 0 |
| 293 | 50 | 100 | 0 |
|  | 12.5 | 100 | 0 |
| 294 | 50 | 100 | 0 |
|  | 12.5 | 100 | 0 |
| 295 | 50 | 100 | 0 |
|  | 12.5 | 100 | 0 |
| 296 | 50 | 100 | 0 |
|  | 12.5 | 100 | 0 |
| 297 | 50 | 100 | 0 |
|  | 12.5 | 100 | 0 |
| 298 | 100 | 100 | 0 |
|  | 50 | 80 | 0 |
| 299 | 50 | 100 | 0 |
|  | 12.5 | 100 | 0 |
| 300 | 200 | 100 | 0 |
|  | 100 | 91 | 0 |
| 301 | 100 | 100 | 0 |
|  | 50 | 84 | 0 |
| 302 | 50 | 100 | 0 |
|  | 12.5 | 100 | 0 |
| 303 | 50 | 100 | 0 |
| 304 | 50 | 100 | 0 |
| 305 | 50 | 100 | 0 |
| 306 | 50 | 100 | 0 |
| 308 | 50 | 100 | 0 |
|  | 12.5 | 100 | 0 |
| 309 | 100 | 100 | 0 |
| 310 | 100 | 86 | 0 |
| 311 | 100 | 100 | 0 |
| 312 | 100 | 80 | 0 |
| 313 | 100 | 78 | 0 |
| 314 | 50 | 100 | 0 |
|  | 25 | 91 | 0 |
| 315 | 100 | 100 | 0 |
|  | 50 | 70 | 0 |
| 316 | 100 | 100 | 0 |
| 317 | 50 | 100 | 0 |
|  | 25 | 76 | 0 |
| 318 | 100 | 100 | 0 |
| 319 | 50 | 100 | 0 |
|  | 25 | 73 | 0 |
| 320 | 50 | 100 | 0 |
|  | 12.5 | 90 | 0 |
| 321 | 100 | 100 | 0 |
| 322 | 100 | 100 | 0 |
| 323 | 50 | 100 | 0 |
|  | 12.5 | 82 | 0 |
| 324 | 100 | 100 | 0 |
| 325 | 100 | 100 | 0 |
| 326 | 100 | 100 | 0 |
| 327 | 50 | 100 | 0 |
|  | 12.5 | 100 | 0 |
| 328 | 100 | 100 | 0 |
| 329 | 100 | 100 | 0 |
| 330 | 50 | 100 | 0 |
|  | 12.5 | 70 | 0 |
| 331 | 50 | 100 | 0 |
|  | 12.5 | 86 | 0 |
| 332 | 100 | 100 | 0 |
|  | 50 | 94 | 0 |
|  | 12.5 | 84 | 0 |
| 333 | 100 | 100 | 0 |
| 334 | 100 | 100 | 0 |
| 335 | 100 | 100 | 0 |
|  | 50 | 94 | 0 |
|  | 25 | 83 | 0 |
| 336 | 100 | 100 | 0 |
|  | 50 | 91 | 0 |
|  | 25 | 76 | 0 |
| 337 | 50 | 100 | 0 |
|  | 12.5 | 91 | 0 |
| 338 | 50 | 100 | 0 |
|  | 12.5 | 76 | 0 |
| 339 | 50 | 100 | 0 |
|  | 12.5 | 81 | 0 |
| 340 | 100 | 100 | 0 |
| 341 | 50 | 100 | 0 |
|  | 12.5 | 100 | 0 |
| 342 | 50 | 100 | 0 |
|  | 12.5 | 100 | 0 |
| 343 | 50 | 100 | 0 |
|  | 12.5 | 70 | 0 |
| 344 | 50 | 100 | 0 |
|  | 12.5 | 74 | 0 |
| 345 | 100 | 100 | 0 |
| 346 | 100 | 100 | 0 |
| 347 | 100 | 100 | 0 |
| Comparative chemical (Buthiobate) | 50 | 100 | 0 |
|  | 25 | 100 | 0 |

TABLE 3-continued

| | (Cucumber powdery mildew) | | |
|---|---|---|---|
| Compound No. | Concentration of spray liquid (ppm) | Control value (%) | Degree of phytotoxicity |
| | 12.5 | 95 | 0 |
| Non-treated | — | 0 | — |

(Note) Buthiobate

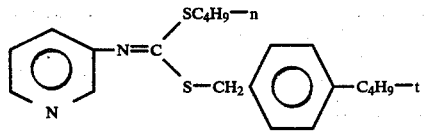

TEST EXAMPLE 3

Test for the control effect on barley powdery mildew

Over the first-leaf stage seedlings of barley (variety: Azuma golden) soil-cultured in a porcelain pot of 9 cm in diameter in a greenhouse was sprayed a solution of a wettable powder diluted to a predetermined concentration at a rate of 10 ml per 2 pots. Next day, the spore of powdery mildew preliminarily outbroken on the leaf of barley was inoculated by scattering over the leaf of barley. Seven days after the inoculation, the number of lesions was investigated and the control value (%) was calculated by the below-defined expression. Phytotoxicity against the barley plant was at the same time investigated by the same fixed numeral scale as used in the Test Example 1.

$$\text{Control value (\%)} = \left(1 - \frac{\text{Number of lesions per leaf in treated plot}}{\text{Number of lesions per leaf in blank plot}}\right) \times 100$$

The results thus obtained are as shown in Table 4.

TABLE 4

| | (Barley powdery mildew) | | |
|---|---|---|---|
| Compound No. | Concentration of spray liquid (ppm) | Control value (%) | Degree of phytotoxicity |
| 1 | 20 | 100 | 0 |
| | 5 | 100 | 0 |
| 2 | 20 | 100 | 0 |
| | 5 | 91 | 0 |
| 3 | 20 | 100 | 0 |
| | 5 | 100 | 0 |
| 4 | 20 | 100 | 0 |
| | 5 | 100 | 0 |
| 5 | 20 | 100 | 0 |
| | 5 | 90 | 0 |
| 6 | 20 | 100 | 0 |
| | 5 | 100 | 0 |
| 7 | 20 | 100 | 0 |
| | 5 | 82 | 0 |
| 8 | 20 | 100 | 0 |
| | 5 | 100 | 0 |
| 9 | 20 | 100 | 0 |
| | 5 | 75 | 0 |
| 10 | 20 | 100 | 0 |
| | 5 | 93 | 0 |
| 11 | 20 | 100 | 0 |
| | 5 | 70 | 0 |
| 12 | 20 | 98 | 0 |
| | 5 | 69 | 0 |
| 13 | 20 | 100 | 0 |
| | 5 | 98 | 0 |
| 14 | 20 | 100 | 0 |
| | 5 | 100 | 0 |
| 15 | 20 | 100 | 0 |
| | 5 | 70 | 0 |
| 16 | 20 | 100 | 0 |
| | 5 | 100 | 0 |
| 17 | 20 | 100 | 0 |
| | 5 | 100 | 0 |
| 18 | 20 | 100 | 0 |
| | 5 | 95 | 0 |
| 19 | 20 | 100 | 0 |
| | 5 | 100 | 0 |
| 20 | 20 | 100 | 0 |
| | 5 | 65 | 0 |
| 21 | 20 | 100 | 0 |
| | 5 | 100 | 0 |
| 22 | 20 | 90 | 0 |
| | 5 | 72 | 0 |
| 23 | 20 | 100 | 0 |
| | 5 | 65 | 0 |
| 24 | 20 | 100 | 0 |
| | 5 | 100 | 0 |
| 25 | 20 | 100 | 0 |
| | 5 | 82 | 0 |
| 26 | 20 | 90 | 0 |
| | 5 | 75 | 0 |
| 27 | 20 | 80 | 0 |
| | 5 | 51 | 0 |
| 28 | 20 | 100 | 0 |
| | 5 | 90 | 0 |
| 29 | 20 | 100 | 0 |
| | 5 | 82 | 0 |
| 30 | 20 | 100 | 0 |
| | 5 | 100 | 0 |
| 31 | 20 | 100 | 0 |
| | 5 | 95 | 0 |
| 32 | 20 | 100 | 0 |
| | 5 | 100 | 0 |
| 33 | 20 | 100 | 0 |
| | 5 | 100 | 0 |
| 34 | 20 | 100 | 0 |
| | 5 | 100 | 0 |
| 35 | 20 | 100 | 0 |
| | 5 | 90 | 0 |
| 36 | 20 | 100 | 0 |
| | 5 | 100 | 0 |
| 37 | 20 | 100 | 0 |
| | 5 | 100 | 0 |
| 38 | 20 | 100 | 0 |
| | 5 | 98 | 0 |
| 39 | 20 | 100 | 0 |
| | 5 | 100 | 0 |
| 40 | 20 | 100 | 0 |
| | 5 | 100 | 0 |
| 41 | 20 | 90 | 0 |
| | 5 | 71 | 0 |
| 42 | 20 | 100 | 0 |
| | 5 | 98 | 0 |
| 43 | 20 | 90 | 0 |
| | 5 | 78 | 0 |
| 44 | 20 | 100 | 0 |
| | 5 | 95 | 0 |
| 45 | 20 | 100 | 0 |
| | 5 | 75 | 0 |
| 46 | 20 | 100 | 0 |
| | 5 | 90 | 0 |
| 47 | 20 | 100 | 0 |
| | 5 | 100 | 0 |
| 48 | 20 | 100 | 0 |
| | 5 | 100 | 0 |
| 49 | 20 | 100 | 0 |
| | 5 | 100 | 0 |
| 50 | 20 | 100 | 0 |
| | 5 | 75 | 0 |
| 51 | 20 | 90 | 0 |
| 52 | 20 | 95 | 0 |
| | 5 | 80 | 0 |
| 53 | 20 | 100 | 0 |
| | 5 | 98 | 0 |
| 54 | 20 | 90 | 0 |

TABLE 4-continued (Barley powdery mildew)

| Compound No. | Concentration of spray liquid (ppm) | Control value (%) | Degree of phytotoxicity |
|---|---|---|---|
| 55 | 20 | 100 | 0 |
| 56 | 20 | 100 | 0 |
|  | 5 | 80 | 0 |
| 57 | 20 | 80 | 0 |
| 58 | 20 | 100 | 0 |
|  | 5 | 100 | 0 |
| 59 | 20 | 100 | 0 |
|  | 5 | 100 | 0 |
| 60 | 20 | 100 | 0 |
|  | 5 | 91 | 0 |
| 61 | 20 | 100 | 0 |
|  | 5 | 70 | 0 |
| 62 | 20 | 100 | 0 |
|  | 5 | 100 | 0 |
| 63 | 20 | 100 | 0 |
| 64 | 20 | 90 | 0 |
| 65 | 20 | 100 | 0 |
|  | 5 | 100 | 0 |
| 66 | 20 | 80 | 0 |
| 67 | 20 | 100 | 0 |
|  | 5 | 82 | 0 |
| 280 | 20 | 100 | 0 |
|  | 5 | 100 | 0 |
| 281 | 20 | 100 | 0 |
|  | 5 | 100 | 0 |
| 282 | 20 | 100 | 0 |
|  | 5 | 100 | 0 |
| 283 | 20 | 100 | 0 |
|  | 5 | 100 | 0 |
| 284 | 20 | 100 | 0 |
|  | 5 | 93 | 0 |
| 285 | 20 | 85 | 0 |
| 286 | 20 | 100 | 0 |
|  | 5 | 85 | 0 |
| 287 | 20 | 100 | 0 |
|  | 5 | 100 | 0 |
| 288 | 20 | 100 | 0 |
|  | 5 | 100 | 0 |
| 289 | 20 | 100 | 0 |
|  | 5 | 99 | 0 |
| 290 | 20 | 100 | 0 |
|  | 5 | 100 | 0 |
| 291 | 20 | 100 | 0 |
|  | 5 | 100 | 0 |
| 292 | 20 | 100 | 0 |
|  | 5 | 98 | 0 |
| Comparative chemical (Buthiobate) | 20 | 100 | 0 |
|  | 5 | 100 | 0 |
| Non-treated | — | 0 | — |

TEST EXAMPLE 4

Test for the control effect on apple powdery mildew

Over the third-leaf stage of seedlings from seed of apple (variety: Kogyoku) soil-cultured in a porcelain pot of 9 cm in diameter in a greenhouse was sprayed a test solution of the emulsion, which was prepared according the procedure of Example 5, by diluting to a predetermined concentration, at a rate of 30 ml per 4 pots. Next day, the seedlings were inoculated by atomizing with a spore suspension of apple powdery mildew fungus. Ten days after the inoculation, percent lesion area was investigated and the control value (%) was calculated according to the following expression.

$$\text{Control value (\%)} = \left(1 - \frac{\text{Percent lesion area in treated plot}}{\text{Percent lesion area in blank plot}}\right) \times 100$$

The results obtained are as shown in Table 5.

TABLE 5

(Apple powdery mildew)

| Compound No. | Concentration of spray liquid (ppm) | Control value (%) | Degree of phytotoxicity |
|---|---|---|---|
| 1 | 50 | 100 | 0 |
|  | 12.5 | 100 | 0 |
| 2 | 50 | 100 | 0 |
|  | 12.5 | 95 | 0 |
| 3 | 50 | 100 | 0 |
|  | 12.5 | 100 | 0 |
| 4 | 50 | 100 | 0 |
|  | 12.5 | 100 | 0 |
| 5 | 50 | 100 | 0 |
|  | 12.5 | 100 | 0 |
| 6 | 50 | 100 | 0 |
|  | 12.5 | 100 | 0 |
| 7 | 50 | 100 | 0 |
|  | 12.5 | 92 | 0 |
| 8 | 50 | 100 | 0 |
|  | 12.5 | 100 | 0 |
| 9 | 50 | 100 | 0 |
|  | 12.5 | 85 | 0 |
| 10 | 50 | 100 | 0 |
|  | 12.5 | 93 | 0 |
| 11 | 50 | 100 | 0 |
|  | 12.5 | 73 | 0 |
| 12 | 50 | 98 | 0 |
|  | 12.5 | 79 | 0 |
| 13 | 50 | 100 | 0 |
|  | 12.5 | 100 | 0 |
| 14 | 50 | 100 | 0 |
|  | 12.5 | 100 | 0 |
| 15 | 50 | 100 | 0 |
|  | 12.5 | 92 | 0 |
| 16 | 50 | 100 | 0 |
|  | 12.5 | 100 | 0 |
| 17 | 50 | 100 | 0 |
|  | 12.5 | 100 | 0 |
| 18 | 50 | 100 | 0 |
|  | 12.5 | 98 | 0 |
| 19 | 50 | 100 | 0 |
|  | 12.5 | 100 | 0 |
| 20 | 50 | 100 | 0 |
|  | 12.5 | 78 | 0 |
| 21 | 50 | 100 | 0 |
|  | 12.5 | 100 | 0 |
| 22 | 50 | 97 | 0 |
|  | 12.5 | 70 | 0 |
| 23 | 50 | 100 | 0 |
|  | 12.5 | 80 | 0 |
| 24 | 50 | 100 | 0 |
|  | 12.5 | 100 | 0 |
| 25 | 50 | 100 | 0 |
|  | 12.5 | 95 | 0 |
| 26 | 50 | 97 | 0 |
|  | 12.5 | 75 | 0 |
| 27 | 50 | 81 | 0 |
|  | 12.5 | 65 | 0 |
| 28 | 50 | 100 | 0 |
|  | 12.5 | 98 | 0 |
| 29 | 50 | 100 | 0 |
|  | 12.5 | 92 | 0 |
| 30 | 50 | 100 | 0 |
|  | 12.5 | 100 | 0 |
| 31 | 50 | 100 | 0 |
|  | 12.5 | 98 | 0 |
| 32 | 50 | 100 | 0 |
|  | 12.5 | 100 | 0 |
| 33 | 50 | 100 | 0 |
|  | 12.5 | 100 | 0 |
| 34 | 50 | 100 | 0 |
|  | 12.5 | 100 | 0 |

TABLE 5-continued (Apple powdery mildew)

| Compound No. | Concentration of spray liquid (ppm) | Control value (%) | Degree of phytotoxicity |
|---|---|---|---|
| 35 | 50 | 100 | 0 |
|  | 12.5 | 95 | 0 |
| 36 | 50 | 100 | 0 |
|  | 12.5 | 100 | 0 |
| 37 | 50 | 100 | 0 |
|  | 12.5 | 100 | 0 |
| 38 | 50 | 100 | 0 |
|  | 12.5 | 95 | 0 |
| 39 | 50 | 100 | 0 |
|  | 12.5 | 100 | 0 |
| 40 | 50 | 100 | 0 |
|  | 12.5 | 98 | 0 |
| 41 | 50 | 93 | 0 |
|  | 12.5 | 80 | 0 |
| 42 | 50 | 100 | 0 |
|  | 12.5 | 100 | 0 |
| 43 | 50 | 95 | 0 |
|  | 12.5 | 80 | 0 |
| 44 | 50 | 100 | 0 |
|  | 12.5 | 98 | 0 |
| 45 | 50 | 100 | 0 |
| 46 | 50 | 100 | 0 |
|  | 12.5 | 92 | 0 |
| 47 | 50 | 100 | 0 |
|  | 12.5 | 100 | 0 |
| 48 | 50 | 100 | 0 |
|  | 12.5 | 100 | 0 |
| 49 | 50 | 100 | 0 |
|  | 12.5 | 100 | 0 |
| 50 | 50 | 100 | 0 |
|  | 12.5 | 81 | 0 |
| 51 | 50 | 93 | 0 |
| 52 | 50 | 98 | 0 |
|  | 12.5 | 83 | 0 |
| 53 | 50 | 100 | 0 |
|  | 12.5 | 100 | 0 |
| 54 | 50 | 95 | 0 |
| 55 | 50 | 95 | 0 |
| 56 | 50 | 100 | 0 |
|  | 12.5 | 85 | 0 |
| 57 | 50 | 87 | 0 |
| 58 | 50 | 100 | 0 |
|  | 12.5 | 95 | 0 |
| 59 | 50 | 100 | 0 |
|  | 12.5 | 100 | 0 |
| 60 | 50 | 100 | 0 |
|  | 12.5 | 88 | 0 |
| 61 | 50 | 100 | 0 |
| 62 | 50 | 100 | 0 |
|  | 12.5 | 100 | 0 |
| 63 | 50 | 100 | 0 |
| 64 | 50 | 95 | 0 |
| 65 | 50 | 100 | 0 |
|  | 12.5 | 100 | 0 |
| 66 | 50 | 83 | 0 |
| 67 | 50 | 100 | 0 |
|  | 12.5 | 91 | 0 |
| 280 | 50 | 100 | 0 |
|  | 12.5 | 95 | 0 |
| 281 | 50 | 100 | 0 |
|  | 12.5 | 97 | 0 |
| 282 | 50 | 100 | 0 |
|  | 12.5 | 100 | 0 |
| 283 | 50 | 100 | 0 |
|  | 12.5 | 89 | 0 |
| 284 | 50 | 100 | 0 |
|  | 12.5 | 96 | 0 |
| 285 | 50 | 93 | 0 |
| 286 | 50 | 100 | 0 |
|  | 12.5 | 92 | 0 |
| 287 | 50 | 100 | 0 |
|  | 12.5 | 100 | 0 |
| 288 | 50 | 100 | 0 |
|  | 12.5 | 100 | 0 |
| 289 | 50 | 100 | 0 |
|  | 12.5 | 100 | 0 |
| 290 | 50 | 100 | 0 |
|  | 12.5 | 100 | 0 |
| 291 | 50 | 100 | 0 |
|  | 12.5 | 99 | 0 |
| 292 | 50 | 100 | 0 |
|  | 12.5 | 93 | 0 |
| 294 | 50 | 100 | 0 |
|  | 12.5 | 97 | 0 |
| 297 | 50 | 100 | 0 |
|  | 12.5 | 95 | 0 |
| 299 | 50 | 100 | 0 |
|  | 12.5 | 100 | 0 |
| Comparative chemical (Buthiobate) | 50 | 100 | 0 |
|  | 12.5 | 95 | 0 |
| Non-treated | — | 0 | — |

TEST EXAMPLE 5

Test for the control of Chinese cabbage root knot disease

A porcelain pot of 9 cm in diameter was filled with a soil infected naturally by Chinese cabbage root knot disease. To the soil was inoculated a Chinese cabbage root knot suspension prepared by grinding the refrigerated root knot and diluting same with water, in order to accelerate the outbreak of disease. Then the wettable powder prepared by the procedures of Example 4 was poured as a solution in water to the surface of the soil at the rate of 3 l/m². Three hours later, 4 (four) seedlings of Chinese cabbage (variety: Sengoku Hakusai) were transplanted to one pot and then cultivated for 40 days. The degree of infection was investigated according to the below-mentioned standard, and the control value (%) was calculated by the below-defined expression.

$$\text{Control value (\%)} = \frac{\Sigma \text{(Index by degree)} \times \text{(Number of infected stocks by degree)}}{4 \times \text{(Number of investigated stocks)}} \times 100$$

Index by degree:
  4: Outbreak of root knots was observed in the overall portion of the root and enlargement of the roots was visible
  3: Outbreak of root knots was observed in more than 50% of roots
  2: Outbreak of root knots was observed in not more than 50% of roots
  1: Outbreak of root knots was observed in not more than 10% of roots
  0: None $$\text{Control value (\%)} = \frac{\text{(Degree of infection in treated pot)}}{\text{(Degree of infection in blank pot)}} \times 100$$

The phytotoxicity against Chinese cabbage plants also was investigated by the same procedures as in Test Example 1.

The results are as shown in Table 6.

TABLE 6
(Chinese cabbage root knot disease)

| Compound No. | Concentration of spray liquid (ppm) | Control value (%) | Degree of phytotoxicity |
|---|---|---|---|
| 1 | 1 | 92 | 0 |
| 2 | 1 | 90 | 0 |
| 3 | 1 | 100 | 0 |
| 4 | 1 | 100 | 0 |
| 5 | 1 | 93 | 0 |
| 6 | 1 | 98 | 0 |
| 7 | 1 | 95 | 0 |
| 8 | 1 | 91 | 0 |
| 9 | 1 | 90 | 0 |
| 10 | 1 | 99 | 0 |
| 11 | 1 | 97 | 0 |
| 12 | 1 | 92 | 0 |
| 13 | 1 | 90 | 0 |
| 14 | 1 | 100 | 0 |
| 15 | 1 | 96 | 0 |
| 16 | 1 | 90 | 0 |
| 17 | 1 | 100 | 0 |
| 18 | 1 | 97 | 0 |
| 19 | 1 | 97 | 0 |
| 20 | 1 | 93 | 0 |
| 21 | 1 | 100 | 0 |
| 22 | 1 | 94 | 0 |
| 23 | 1 | 98 | 0 |
| 24 | 1 | 99 | 0 |
| 25 | 1 | 95 | 0 |
| 26 | 1 | 100 | 0 |
| 27 | 1 | 100 | 0 |
| 28 | 1 | 100 | 0 |
| 29 | 1 | 100 | 0 |
| 30 | 1 | 100 | 0 |
| 31 | 1 | 97 | 0 |
| 32 | 1 | 92 | 0 |
| 33 | 1 | 100 | 0 |
| 34 | 1 | 91 | 0 |
| 35 | 1 | 93 | 0 |
| 36 | 1 | 100 | 0 |
| 37 | 1 | 100 | 0 |
| 38 | 1 | 100 | 0 |
| 39 | 1 | 100 | 0 |
| 40 | 1 | 100 | 0 |
| 41 | 1 | 98 | 0 |
| 42 | 1 | 100 | 0 |
| 43 | 1 | 100 | 0 |
| 44 | 1 | 100 | 0 |
| 66 | 1 | 100 | 0 |
| 67 | 1 | 100 | 0 |
| 280 | 1 | 100 | 0 |
| 281 | 1 | 100 | 0 |
| 282 | 1 | 100 | 0 |
| 283 | 1 | 100 | 0 |
| 284 | 1 | 100 | 0 |
| 287 | 1 | 100 | 0 |
| Comparative chemical (PCNB) | 5 | 88 | 0 |
|  | 1 | 5 | 0 |
| Non-treated | — | 0 | — |

(Note) PCNB

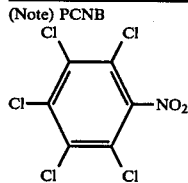

What we claim is:

1. A thiophene compound of the general formula (I)

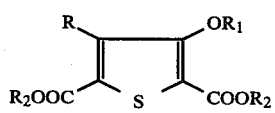

In the general formula:
R is $C_{1-4}$-alkyl; $R_1$ is

wherein $R_3$ is $C_{1-4}$-alkyl, halogen-substituted $C_{1-4}$-alkyl, $C_{2-4}$-alkenyl, $C_{3-8}$-cycloalkyl, $C_{1-4}$-alkoxy-$C_{1-4}$-alkyl, $C_{1-4}$-alkylthio-$C_{1-4}$-alkyl, $C_{1-4}$-alkoxycarbonyl-$C_{1-4}$-alkyl, $C_{1-10}$-alkoxy, $C_{1-4}$-alkynyloxy, styryl, α-phenoxyethyl, thienyl, furyl, 2,3-dibromopropyloxy, a group

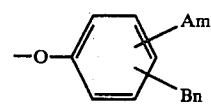

(wherein A and B individually are halogen, $C_{1-4}$-alkyl, methoxy or methylthio, and m and n individually are 0 or 1 with the proviso m+n cannot exceed (2), mono-$C_{1-4}$-alkylamino, di-$C_{1-4}$-alkylamino, mono-$C_{3-8}$-cycloalkylamino, monoaralkylamino, diphenylamino, a group

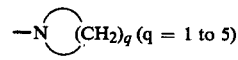

which may be substituted with one or two $C_{1-4}$-alkyl;

a group

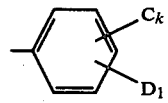

(wherein C is a halogen atom, D is $C_{1-4}$-alkyl, $C_{1-4}$-alkoxy, $C_{1-4}$-alkylcarboxy, nitro or cyano, k is 0, 1 or 2 and 1 is 0, 1, 2 or 3);
$C_{1-4}$-alkylthio; $C_{1-4}$-alkenylthio; $C_{1-4}$-alkoxycarbonyl-$C_{1-4}$-alkylthio; aralkylthio or $C_{1-4}$-alkyl-substituted aralkylthio; aralkyl which phenyl portion may be substituted with halogen or $C_{1-4}$-alkoxy;

a group

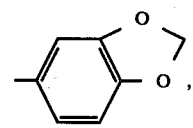

phenoxy-$C_{1-4}$-alkyl which phenyl portion may be substituted with halogen; pyridine-4-yl; or a group

wherein $R_4$ is $C_{1-6}$-alkyl, di-$C_{1-4}$-alkylamino or a group

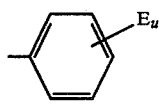

(in which E is halogen or $C_{1-4}$-alkyl and u is 0 or 1);
$R_2$ is $C_{1-4}$-alkyl or $C_{2-4}$-alkenyl; provided that:
(a) when $R_3$ is mono-$C_{3-8}$-cycloalkylamino, $R_2$ represents $C_{1-4}$-alkoxy-$C_{1-4}$-alkyl, aralkyl, phenoxy-$C_{1-4}$-alkyl or $C_{2-4}$-alkynyl;
(b) when $R_3$ is

$R_2$ represents $C_{1-4}$-alkoxy-$C_{1-4}$-alkyl or aralkyl;
(c) when $R_3$ is

$R_2$ represents $C_{3-8}$-cycloalkyl; and
(d) when $R_3$ is $C_{1-4}$-alkylthio, $R_2$ represents $C_{1-4}$-alkoxy-$C_{1-4}$-alkyl, aralkyl or phenoxy-$C_{1-4}$-alkyl.

2. A fungicidal composition which comprises in association with a carrier or diluent a fungicidally active amount of a compound of the general formula (I)

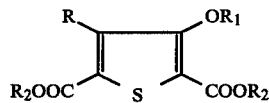

In the general formula:
R is $C_{1-4}$-alkyl;
$R_1$ is

wherein $R_3$ is $C_{1-4}$-alkyl, halogen-substituted $C_{1-4}$-alkyl, $C_{2-4}$-alkenyl, $C_{3-8}$-cycloalkyl, $C_{1-4}$-alkoxy-$C_{1-4}$-alkyl, $C_{1-4}$-alkylthio-$C_{1-4}$-alkyl, $C_{1-4}$-alkoxycarbonyl-$C_{1-4}$-alkyl, $C_{1-10}$-alkoxy, $C_{1-4}$-alkynyloxy, styryl, α-phenoxyethyl, thienyl, furyl, 2,3-dibromopropyloxy,
a group

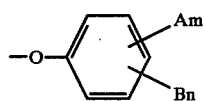

(wherein A and B individually are halogen, $C_{1-4}$-alkyl, methoxy or methylthio, and m and n individually are 0 or 1 with the proviso m+n cannot exceed 2), mono-$C_{1-4}$-alkylamino, di-$C_{1-4}$-alkylamino, mono-$C_{3-8}$-cycloalkylamino, monoaralkylamino, diphenylamino,
a group

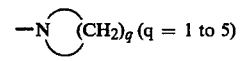

which may be substituted with one or two $C_{1-4}$-alkyl;
a group

(wherein C is a halogen atom, D is $C_{1-4}$-alkyl, $C_{1-4}$-alkoxy, $C_{1-4}$-alkylcarboxy, nitro or cyano, k is 0, 1 or 2 and 1 is 0, 1, 2 or 3);
$C_{1-4}$-alkylthio; $C_{1-4}$-alkenylthio; $C_{1-4}$-alkoxycarbonyl-$C_{1-4}$-alkylthio; aralkylthio or $C_{1-4}$-alkyl-substituted aralkylthio; aralkyl which phenyl portion may be substituted with halogen or $C_{1-4}$-alkoxy;
a group

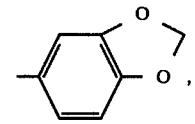

phenoxy-$C_{1-4}$-alkyl which phenyl portion may be substituted with halogen; pyridine-4-yl; or
a group

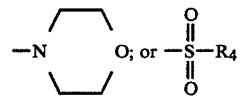

wherein $R_4$ is $C_{1-6}$-alkyl, di-$C_{1-4}$-alkylamino or
a group

(in which E is halogen or $C_{1-4}$-alkyl and u is 0 or 1);
$R_2$ is $C_{1-4}$-alkyl or $C_{2-4}$-alkenyl; provided that:
(a) when $R_3$ is mono-$C_{3-8}$-cycloalkylamino, $R_2$ represents $C_{1-4}$-alkoxy-$C_{1-4}$-alkyl, aralkyl, phenoxy-$C_{1-4}$-alkyl or $C_{2-4}$-alkynyl;
(b) when $R_3$ is

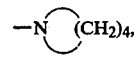

$R_2$ represents $C_{1-4}$-alkoxy-$C_{1-4}$-alkyl or aralkyl;
(c) when $R_3$ is

$R_2$ represents $C_{3-8}$-cycloalkyl; and
(d) when $R_3$ is $C_{1-4}$-alkylthio, $R_2$ represents $C_{1-4}$-alkoxy-$C_{1-4}$-alkyl, aralkyl or phenoxy-$C_{1-4}$-alkyl.

* * * * *